US006653134B2

(12) United States Patent
Prockop et al.

(10) Patent No.: US 6,653,134 B2
(45) Date of Patent: Nov. 25, 2003

(54) ISOLATED STROMAL CELLS FOR USE IN THE TREATMENT OF DISEASES OF THE CENTRAL NERVOUS SYSTEM

(75) Inventors: Darwin J. Prockop, Philadelphia, PA (US); David G. Stokes, Willow Grove, PA (US); S. Ausim Azizi, Philadelphia, PA (US)

(73) Assignee: CP Hahnemann University, Philadelphia, PA (US)

( * ) Notice: Subject to any disclaimer, the term of this patent is extended or adjusted under 35 U.S.C. 154(b) by 0 days.

(21) Appl. No.: 09/028,395

(22) Filed: Feb. 24, 1998

(65) Prior Publication Data

US 2003/0039639 A1 Feb. 27, 2003

Related U.S. Application Data

(63) Continuation-in-part of application No. PCT/US96/04407, filed on Mar. 28, 1996, which is a continuation of application No. 08/412,066, filed on Mar. 28, 1995, now Pat. No. 5,716,616.
(60) Provisional application No. 60/006,627, filed on Nov. 13, 1995.

(51) Int. Cl.$^7$ ................................................ C12N 5/00
(52) U.S. Cl. ...................... 435/377; 435/366; 435/368; 435/372; 435/373
(58) Field of Search .............................. 435/455, 366, 435/368, 372, 373, 377; 424/93.21, 93.7, 570, 577

(56) References Cited

U.S. PATENT DOCUMENTS

| | | | |
|---|---|---|---|
| 4,391,909 A | 7/1983 | Lim | 435/178 |
| 4,806,355 A | 2/1989 | Goosen et al. | 424/424 |
| 4,902,295 A | 2/1990 | Walthall et al. | 623/11 |
| 4,904,259 A | 2/1990 | Itay | 623/16 |
| 4,942,129 A | 7/1990 | Goosen et al. | 435/182 |
| 4,997,443 A | 3/1991 | Walthall et al. | 623/11 |
| 5,082,670 A | 1/1992 | Gage et al. | 424/520 |
| 5,314,471 A | 5/1994 | Brauker et al. | 623/11 |
| 5,334,640 A | 8/1994 | Desai et al. | 524/56 |
| 5,344,454 A | 9/1994 | Clarke et al. | 623/11 |

FOREIGN PATENT DOCUMENTS

EP  0 381 490   8/1990

OTHER PUBLICATIONS

D. Prockop, Science, 276:71–74, 1997.*
Gerson, Nature Medicine, 5:262–264, 1999.*
Sanberg et al., Nucleic Acids Symp. Ser., 38:139–142, 1998.*
Sabate et al., Clinical Neuroscience, 3:317–321, 1996.*
Eglitis et al., Proc. Natl. Acad. Sci., USA, 94:4080–4085, 1997.*
Pereira et al., Proc. natl. Acad. Sci., USA, 92:4857–4861, 1995.*
Friedmann, TIG, 10:210–214, 1994.*
Banati et al., 1991, Journal of Neuroscience Research 30:593–600.
Jaiswal et al., 1997, Journal of Cellular Biochemistry 64:295–312.
Sievers et al., 1994, Glia 12:245–258.
Andsberg et al, 2002, Neurobiol Dis 9:187–204.
Ankeny et al, 2001 Annual Meeting of the Society of Neuroscience.
Bjorklund et al, 1992, Curr Opin Neurobiol 2:683–9.
Bjorklund et al, 1980, Brain Res 199:307–33.
Chopp et al., 2000, Neuroreport 11:3001–3005.
Craddock, 2000, Lancet Oncol. 1:227–234.
Danisi et al., 2002, Geriatrics 57:46–50.
De Cristobal, et al., 2001, J. Neurochem 79:456–459.
Dogne et al., 2002, Curr Med Chem 9:577–589.
Dumont et al., 2001, Clin Neuropharmacol 24:265–279.
Dunnett et al., 1981, Brain Res 229:209–217.
During et al., 1994, Science 266:1399–1403.
Himes et al., 2001, J Neurosci Res 65:549–564.
Hofstetter et al., 2002, Proc Natl Acad Sci USA 99:2199–2204.
Honmou et al., 2001, Annual Meeting of the Society of Neuroscience.
Keating et al., 1990, Exp Hematol 18:99–102.
Kopen et al., 1999, Proc Natl Acad Sci USA 96:10711–10716.
Kotton et al., 2001, Development 128:5181–5188.
Labombarda et al., 2002, J Neurotrauma 19:343–355.
Lopez–Lozano et al., 1997, Transplant Proc 29:977–980.
Lu et al., 2001, J Neurotrauma 18:813–819.
Mandel et al., 1998, J Neurosci 18:4271–4284.
Piccini et al., 1999, Nat Neurosci 2:1047–1048.
Piccini et al., 2000, Ann Neurol 48:689–695.
Saba et al., 2002, J Hematother Stem Cell Res 11:377–387.
Schwarz et al., 1999, Human Gene Therapy 10:2539–2549.
Schwarz et al., 2001, Gene Therapy 8:1214–1223.
Schwarz et al., 2001, ISHAGE 2001, Jun. 14–17, 2001.
Ungerstedt et al., 1974, Advances in Neurobiology 5:421–426.
Wictorin et al., 1992, J Comp Neurol 323:475–494.

(List continued on next page.)

Primary Examiner—Jeffrey Siew
Assistant Examiner—Richard Schnizer
(74) Attorney, Agent, or Firm—Morgan, Lewis & Bockius, LLP

(57) ABSTRACT

Methods of treating a human patient having a disease, disorder or condition of the central nervous system are disclosed. The methods include obtaining a bone marrow sample from a human donor, isolating stromal cells from the bone marrow sample, and administering the isolated stromal cells to the central nervous system of the human patient, wherein the presence of the isolated stromal cells in the brain effects treatment of the disease, disorder or condition. Stromal cells which are isolated may be cultured in vitro, they may be genetically engineered to produce therapeutic compounds, and/or they may be pre-differentiated prior to administration into the central nervous system.

2 Claims, 7 Drawing Sheets

OTHER PUBLICATIONS

Widner et al., 1992, N Engl J Med 327:1589–1590 and 1591–1592.
Woodbury et al., 2000, J Neurosci Res 61:364–370.
Wu et al., 2002, Neuroscience Letters 318:81–84.
Rosenberg et al., 1988, Science 242:1575–1578.
Gage et al., 1991, Trends in Neurosciences 14:328–333.
Freed et al., 1990, Progress in Brain Research 82:11–21.
Wolff et al., 1989, Proc. Natl. Acad. Sci., 86:9011–9014.
Gage et al., 1987, Neuroscience 23:795–807.
Sloan et al., 1991, Trends in Neurosciences 14:341–346.
El–Badri–Dajani et al., 1996, Cell Transplantation 5:5S2–36.
Denizot et al., 1998, Biochimica et Biophysica 1402:209–215.
Huss et al., 1995, Cell Transplantation, 4:483–491.
Kadiyala et al., 1997, Cell Transplantation 6:125–134.
Sykes and Sachs, 1990, Immunology 2:401–417.
Arner, P., 1995, N. England J. Med. 333–382.
Coccia, P.F. et al, 1980, New England Journal of Medicine, 302,13:702–707.
Emorine, L. et al., 1994, Trends Pharmacol. Sci., 15,3.
Flier, J.S., 1995, Cell, 80:15.
Lowell, B.B. et al., 1995, J. Clin. Invest., 95:923.
Miller, A.D. and Rosman, G.J. 1989 Bio Techniques 7:980–990.
Morrison et al., 1994, Nature 367:284–287.
Nakagawa, T., et al., 1993, Arthritis and Rheumatism, 36,2:263–268.
Rink, T.J. et al., 1994, Nature, 372–406.
Ala–Kokko et al., 1991, J. Biol. Chem. 266:14175–14178.
Andersson et al., 1993, Int. J. Dev. Neurosci.11:555–568.
Andreason et al., 1988, BioTechniques 6:650–660.
Anklesaria, 1987, PNAS USA 84:7681–7685.
Applebaum et al., 1992, Blood 80(6):1608–1613.
Azizi, 1996, Ann. Neurol. (suppl)121:T236.
Benayahu et al., 1989, J. Cell Physiol. 140:1–7.
Bennett et al., 1991, J. Cell. Sci. 99:131–139.
Beresford et al., 1992, J. Cell. Sci.102:341–351.
Bienzle et al., 1994, Proc. Natl. Acad. Sci USA, 91:350–354.
Bjorklund, 1993, Nature 362:414–415.
Bradham et al., 1994, J. Cell Physiol.158:61–68.
Bruder et al.,1997, J. Cell Biochem. 64:278–294.
O'Hara et al., 1991, Exp. Hemat. 19:878–881.
Ohgushi et al., 1989, Acte. Orthop. Scand. 60:334–339.
Olson, 1997, Nature Med. 3:1329–1335.
Owen et al., 1988, in Cell and Molecular Biology of Vertebrate Hard Tissues, Ciba Foundation Symposium 136, Chichester, UK, pp. 42–60.
Pereira et al., 1995, Proc. Natl. Acad. Sci. USA 92:4857–4861.
Pereira et al., 1983, J. Clin. Ivest. 91:709–716.
Pereira et al., 1998, Proc. Natl. Acad. Sci. 95:1142–1147.
Piersma et al. 1983, Brit J. Hematol. 94:285–290.
Piersma et al., 1985, Exp. Hematol 13:237–243.
Prockop, 1997, Science 276:71–74.
Rosenstein, 1995, Exp. Neurol. 133:1–6.
Sanberg et al., 1997, Nature Med. 3:1129–1132.
Simmons et al., 1991, Blood 78:55–62.
Smith et al., 1993, Mature Genet. 5:397–402.
Sokolov et al., 1995, J. Biol. Chem. 270:9622–9629.
Sokolov et al., 1993, Biochemistry 32:9242–9249.
Spencer et al., 1992, N. Engl. J. Med. 327:1541–1548.
Stewart et al. 1993, Blood 81:2566–2571.
Toneguzzo et al., 1986, Mol. Call. Biol. 6:703–706.
Turner et al., 1993, Neurosurg. 33:1031–1037.
Wakitani et al., 1994, J. Bone & Surg. 76A:579–592.
Zhou et al., 1992, J. Comp. Neurol. 317:145–155.

* cited by examiner

Diffusion Chamber

ISOLATED STROMAL CELLS FOR USE IN THE TREATMENT OF DISEASES OF THE CENTRAL NERVOUS SYSTEM

CROSS-REFERENCE TO RELATED APPLICATIONS

The present application is a continuation-in-part of PCT Application No. PCT/US96/04407, filed on Mar. 28, 1996, which is a continuation of U.S. application Ser. No. 08/412,066, filed on Mar. 28, 1995, now U.S. Pat. No. 5,716,616, and which is also entitled to priority under 35 U.S.C. 119(e) to U.S. Provisional Application No. 60/006,627, filed on Nov. 13, 1995.

STATEMENT REGARDING FEDERALLY SUPPORTED RESEARCH AND DEVELOPMENT

This work was supported in part by U.S. Government funds (National Institutes of Health, Grant No. AR44210), and the U.S. Government may therefore have certain rights in the invention.

FIELD OF THE INVENTION

The invention relates to compositions and methods of treating a mammal suffering from a disease, disorder or a condition associated with the central nervous system, using isolated stromal cells.

BACKGROUND OF THE INVENTION

Neurological damage in a mammal having as its genesis trauma, tumor formation or a genetic or other component, is very difficult to treat and/or reverse in the mammal. One treatment for neurological damage to the central nervous system is neurotransplantation. Over the last few decades, neurotransplantation has been used to explore the development, plasticity, and regeneration of the central nervous system (McKay, 1997, Science 276:66–71). Also, neurotransplantation has been used to effect the repair and functional restoration of diseased and damaged nervous tissues (Bjorklund, 1993, Nature 362:414–415; Olson, 1997, Nature Med. 3:1329–1335; Spencer et al., 1992, N. Engl. J. Med. 327:1541–1548: Freed et al., 1992, N. Engl. J. Med 327:1549–1555; Kordower et al., 1995, N. Engl. J. Med. 332:1118–1124; Defer et al., 1996, Brain 119:41–50; Lopez-Lozano et al., 1997, Transp. Proc. 29:977–980; Rosenstein, 1995, Exp. Neurol. 33:106; Turner et al., 1993, Neurosurg. 33:1031–1037; Kang et al., 1993, J. Neurosci. 13:5203–5211; Andersson et al., 1993, Int. J. Dev. Neurosci. 11:555–568; Sanberg et al., 1997, Nature Med. 3:1129–1132). In particular, a series of human patients with Parkinson's disease have been treated by neurotransplantation of mesencephalic cells obtained from 6 to 9 week old abortuses of human fetuses (Spencer et al., 1992, N. Engl. J. Med. 327:1541–1548: Freed et al., 1992, N. Engl. J. Med 327:1549–1555; Kordower et al., 1995, N. Engl. J. Med. 332:1118–1124; Defer et al., 1996, Brain 119:41–50; Lopez-Lozano et al., 1997, Transp. Proc. 29:977–980). Some of the patients exhibited significant improvement both in clinical symptoms and in the synthesis of dopamine, as assessed by fluorodopa uptake using positron-emission tomography (Spencer et al., 1992, N. Engl. J. Med. 327:1541–1548: Freed et al., 1992, N. Engl. J. Med 327:1549–1555; Kordower et al., 1995, N. Engl. J. Med. 332:1118–1124; Defer et al., 1996, Brain 119:41–50). However, the process of obtaining fetal tissue for therapeutic uses has presented major logistic and ethical barriers (Rosenstein, 1995, Exp. Neurol. 33:106; Turner et al., 1993, Neurosurg. 33:1031–1037). Also, only about 5 to 10% of dopaminergic neurons survive, apparently because of adverse immune reaction to the same (Lopez-Lozano et al., 1997, Transp. Proc. 29:977–980) and because the fetal tissue is primarily dependent on lipid instead glycolytic metabolism (Rosenstein, 1995, Exp. Neurol. 33:106). For these reasons, attempts have been made to develop alternative cells such as fibroblasts (Kang et al., 1993, J. Neurosci. 13:5203–5211), fetal astrocytes (Andersson et al., 1993, Int. J. Dev. Neurosci. 11:555–568), and sertoli cells (Sanberg et al., 1997, Nature Med. 3:1129–1132) which are suitable for neurotransplantation.

In order to treat diseases, disorders, or conditions of the central nervous system, such as for example brain tumors, brain trauma, Huntington's disease, Alzheimer's disease, Parkinson's disease, and spinal cord injury, by transplantation, donor cells should be easily available, capable of rapid expansion in culture, immunologically inert, capable of long term survival and integration in the host brain tissue, and amenable to stable transfection and long-term expression of exogenous genes (Bjorklund, 1993, Nature 362:414–415; Olson, 1997, Nature Med. 3:1329–1335). Donor cells meeting these criteria are not currently available.

In addition to the hematopoietic stem cells, bone marrow contains stem-like precursors for non-hematopoietic cells, such as osteoblasts, chondrocytes, adipocytes and myoblasts (Owen et al., 1988, in Cell and Molecular Biology of Vertebrate Hard Tissues, Ciba Foundation Symposium 136, Chichester, UK, pp. 42–60; Caplan, 1991, J. Orthop. Res. 9:641–650; Prockop, 1997, Science 276:71–74). Non-hematopoietic precursors of the bone marrow have been variously referred to as colony-forming-unit-fibroblasts, mesenchymal stem cells, and marrow stromal cells (MSCs).

MSCs are mesenchymal precursor cells (Friedenstein et al., 1976, Exp. Hemat. 4:267–274) that are characterized by their adherence properties when bone marrow cells are removed from a mammal and are transferred to plastic dishes. Within about four hours, MSCs adhere to the plastic and can thus be isolated by removing non-adherent cells from the dishes. Bone marrow cells, i.e., MSCs, that tightly adhere to plastic have been studied extensively (Castro-Malaspina et al., 1980, Blood 56:289–30125; Piersma et al., 1985, Exp. Hematol 13:237–243; Simmons et al., 1991, Blood 78:55–62; Beresf ord et al., 1992, J. Cell. Sci. 102:341–3 51; Liesveld et al., 1989, Blood 73:1794–1800; Liesveld et al., Exp. Hematol 19:63–70; Bennett et al., 1991, J. Cell. Sci. 99:131–139). The terms "MSCs" and "stromal cells" are used interchangeably herein.

Stromal cells are believed to participate in the creation of the microenvironment within the bone marrow in vivo. When isolated, stromal cells are initially quiescent but eventually begin dividing so that they can be cultured in vitro. Expanded numbers of stromal cells can be established and maintained. Stromal cells have been used to generate colonies of fibroblastic adipocytic and osteogenic cells when cultured under appropriate conditions. They can also be made to differentiate into cartilage cells and myoblasts. If the adherent cells are cultured in the presence of hydrocortisone or other selective conditions, populations enriched for hematopoietic precursors or osteogenic cells are obtained (Carter et al., 1992, Blood 79:356–364 and Bienzle et al., 1994, Proc. Natl. Acad. Sci USA, 91:350–354).

There are several examples of the use of stromal cells for treatment of disease. For example, European Patent EP 0,381,490, discloses gene therapy using stromal cells. In particular, a method of treating hemophilia is disclosed. Stromal cells have been used to produce fibrous tissue, bone or cartilage when implanted into selective tissues in vivo (Ohgushi et al., 1989, Acte. Orthop. Scand. 60:334–339; Nakahara et al., 1992, J. Orthop. Res. 9:465–476; Niedzwiedski et al., 1993, Biomaterials 14:115–121; and Wakitani et al., 1994, J. Bone & Surg. 76A:579–592). In some reports, stromal cells have been used to generate bone or cartilage in vivo when implanted subcutaneously with a porous ceramic (Ohgushi, et al., 1989, Acta. Orthop. Scand. 60:334–339), intraperitoneally in a diffusion chamber (Nakahara et al., 1991, J. Orthop. Res. 9:465–476), percutaneously into a surgically induced bone defect (Niedzwiedski, et al., 1993, Biomaterials 14: 115–121), or transplanted within a collagen gel to repair a surgical defect in a joint cartilage (Wakitani et al., 1994, J. Bone Surg. 76A: 579–592). Piersma et al. (1983, Brit. J. Hematol. 94:285–290) disclose that after intravenous bone marrow transplantation, the fibroblast colony-forming cells which make up the hemopoietic stroma lodge and remain in the host bone marrow. Stewart et al. (1993, Blood 81:2566–2571) recently observed that unusually large and repeated administrations of whole marrow cells produced long-term engraftment of hematopoietic precursors into mice that had not undergone marrow ablation. Also, Bienzle et al. (1994, Proc. Natl. Acad. Sci. USA, 91:350–354) successfully used long-term bone marrow cultures as donor cells to permanently populate hematopoietic cells in dogs without marrow ablation. In some reports, stromal cells were used either as cells that established a microenvironment for the culture of hematopoietic precursors (Anklesaria, 1987, PNAS USA 84:7681–7685) or as a source of an enriched population of hematopoietic stem cells (Kiefer, 1991, Blood 78(10):2577–2582).

Given the paucity of successful treatments for diseases, disorders and conditions of the central nervous system, there remains a need for additional methods of treating patients affected by a disease, disorder, or condition of the central nervous system. The present invention satisfies this need and overcomes the deficiencies of prior art treatments.

SUMMARY OF THE INVENTION

The invention relates to a method of treating a human patient having a disease, disorder or condition of the central nervous system. The method comprises obtaining a bone marrow sample from a human donor, isolating stromal cells from the bone marrow sample, and administering the isolated stromal cells to the central nervous system of the human patient, wherein the presence of the isolated stromal cells in the central nervous system effects treatment of the disease, disorder or condition.

In one aspect, the human donor is not suffering from a disease, disorder or condition of the central nervous system and the human donor is synergeneic with the patient.

In another aspect, the human donor is the human patient.

In yet another aspect, the disease, disorder or condition of the central nervous system is selected from the group consisting of a genetic disease, a tumor, trauma and stroke.

In a preferred embodiment, the disease, disorder or condition is injury to the tissues or cells of the central nervous system. In another preferred embodiment, the disease, disorder or condition is a brain tumor.

In another aspect, the isolated stromal cells administered to the central nervous system remain present or replicate in the central nervous system.

In a further aspect, prior to administering the isolated stromal cells, the cells are cultured in vitro.

In yet a further aspect, prior to administering the isolated stromal cells, the isolated stromal cells are transfected with an isolated nucleic acid encoding a therapeutic protein, wherein when the protein is expressed in the cells the protein serves to effect treatment of the disease, disorder or condition.

In a preferred embodiment, the therapeutic protein is selected from the group consisting of a cytokine, a chemokine and a neurotrophin.

In yet another aspect, prior to administering the isolated stromal cells, the isolated stromal cells are transfected with an isolated nucleic acid encoding a therapeutic protein wherein when such protein is secreted by the cells the protein serves to effect treatment of the disease, disorder or condition.

In a preferred embodiment, the isolated nucleic acid is operably linked to a promoter/regulatory sequence. In yet another preferred embodiment, the therapeutic protein is selected from the group consisting of a cytokine, a chemokine and a neurotrophin. And, in a further preferred embodiment, the isolated nucleic acid is a wild type copy of a mutated, non-functioning or under-expressed gene, wherein the isolated nucleic acid is operably linked to a promoter/regulatory sequence and is expressed in the isolated stromal cells.

In yet another preferred embodiment, the isolated nucleic acid is a wild type copy of a mutated, non-functioning or under-expressed gene, wherein the isolated nucleic acid is operably linked to a promoter/regulatory sequence and is expressed in to generate a protein which is secreted from the isolated stromal cells.

In another aspect of this aspect of the invention, prior to administrating the stromal cells, the cells are pre-differentiated by coculturing the stromal cells in the presence of a substantially homogeneous population of differentiated cells, whereby the stromal cells differentiate and acquire the phenotypic characteristics of the differentiated cells.

In yet another aspect, prior to administration of the isolated stromal cells at least one of the steps of culturing the cells in vitro, introducing isolated nucleic acid into the cells, and pre-differentiating the cells, is performed.

In another aspect, the isolated stromal cells are immunologically isolated.

The invention also relates to a method of directing the differentiation of an isolated stromal cell comprising culturing the isolated stromal cell in the presence of a substantially homogeneous population of differentiated cells whereby the isolated stromal cell differentiates and acquires the phenotypic characteristics of the differentiated cells.

In one aspect of this aspect of the invention, the differentiated cells are astrocytes.

DETAILED DESCRIPTION OF THE INVENTION

Figure 1:
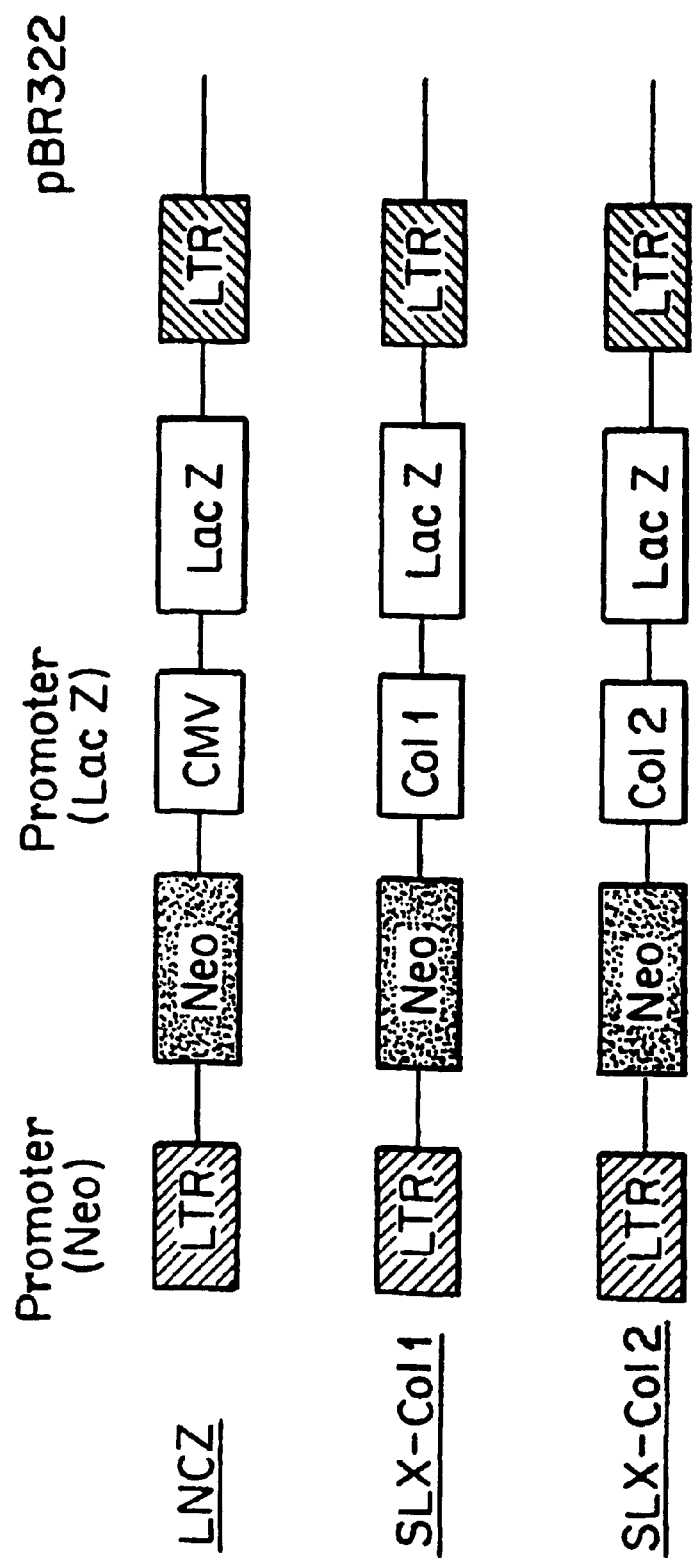
FIG. 1 is a schematic of the retroviral constructs pCMV-lac Z, pCOL1-lac Z, and pCOL2-lac Z. The cassettes of the gene constructs are: LTR-Neo-promoter-Lac Z30 LTR.

The invention includes compositions and methods for treating patients affected by a disease, disorder, or condition of the central nervous system. The composition is isolated marrow cells which may or may not be genetically altered using recombinant DNA technology. The method comprises the steps of obtaining a bone marrow sample from a donor, isolating stromal cells from the bone marrow sample and administering the isolated stromal cells directly into the central nervous system of the patient.

Definitions

As used herein, "central nervous system" should be construed to include brain and/or the spinal cord of a mammal. The term may also include the eye and optic nerve in some instances.

As used herein, "stromal cells", "colony forming fibroblasts", "marrow stromal cells", "adherent cells" and "MSCs" are used interchangeably and are meant to refer to the small fraction of cells in bone marrow which can serve as stem cell like precursors of osteocytes, chondrocytes, and adipocytes and which can be isolated from bone marrow by their ability adhere to plastic dishes. Stromal cells may be derived from any animal. In some embodiments, stromal cells are derived from primates, preferably humans.

As used herein, the term "adherent cells" is meant to refer to stromal cells.

The term "non-adherent cells" as used herein, is meant to refer to hematopoietic precursor cells.

As used herein, the term "disease, disorder or condition of the central nervous system" is meant to refer to a disease, disorder or a condition which is caused by a genetic mutation in a gene that is expressed by cells of the central nervous system such that one of the effects of such a mutation is manifested by abnormal structure and/or function of the central nervous system, such as, for example, neurodegenerative disease or primary tumor formation. Such genetic defects may be the result of a mutated, non-functional or under-expressed gene in a cell of the central nervous system. The term should also be construed to encompass other pathologies in the central nervous system which are not the result of a genetic defect per se in cells of the central nervous system, but rather are the result of infiltration of the central nervous system by cells which do not originate in the central nervous system, for example, metastatic tumor formation in the central nervous system. The term should also be construed to include trauma to the central nervous system induced by direct injury to the tissues of the central nervous system.

As used herein, "a disease, disorder or condition characterized by a gene defect" is meant to refer to a disease, disorder and condition in which a defective gene and/or insufficient gene expression is causally linked to the disease, disorder or condition. Individual who have any of several well known diseases, disorders and conditions characterized by a gene defect can be identified by those having ordinary skill in the art.

As used herein, "a disease, disorder or condition characterized by a defect in a gene which encodes a secreted protein" is meant to refer to a disease, disorder or condition characterized by a gene defect in which the gene that is defective or insufficiently expressed encodes a protein that is abnormally secreted from the cell.

By the term "abnormal secretion" is meant that the protein is processed in the cell in a manner which differs from the normal, i.e., wild type, non-defective protein. For example, the normal protein may be secreted from the cell in a particular structural configuration; abnormal secretion of this protein may occur when the protein is secreted in a different configuration. Further by way of example, when the normal protein is normally secreted from the cell, abnormal secretion of the protein may occur if the protein is not secreted from the cell, or is secreted from the cell at a level which differs markedly, i.e., is higher or lower, from the normal level of secretion of the normal protein.

As used herein, "a disease, disorder or condition which can be treated with a beneficial protein" is meant to refer to a disease, disorder or condition that can be treated or prevented by the presence of a protein which alleviates, reduces, prevents or causes to be alleviated, reduced or prevented, the causes and/or symptoms that characterize the disease, disorder or condition. Diseases, disorders and conditions which can be treated with a beneficial protein include diseases, disorders and conditions characterized by a gene defect as well as those which are not characterized by a gene defect but which nonetheless can be treated or prevented by the presence of a protein which alleviates, reduces, prevents or causes to be alleviated, reduced or prevented, the causes and/or symptoms that characterize the disease, disorder or condition.

As used herein, "beneficial protein" and "heterologous protein" are interchangeable and are meant to refer to a protein which can compensate for the protein encoded by a defective gene and/or insufficient gene expression that is causally linked to the disease or symptoms of the disease, disorder or condition characterized by a gene defect. The presence of the protein alleviates, reduces, prevents or causes to be alleviated, reduced or prevented, the causes and/or symptoms that characterize the disease, disorder or condition.

As used herein, "injury to the tissues or cells of the central nervous system caused by a tumor," is meant to refer to a disease, disorder or a condition of the central nervous system, wherein new growth of tissue occurs, usually in the brain and includes multiplication of cells which is uncontrollable and progressive. The cells which multiply may originate from, or may not originate from the central nervous tissue.

As used herein, "immunologically isolated", "immunologically protected", "immunologically neutralized", and "a manner that physically isolates cells from the recipient's immune system" are meant to refer to the encapsulation, containment or other physical separation of an implanted cell from the body into which it is implanted such that the cell is not exposed to and cannot be eliminated by the immune system of the body, such that cells which are immunologically isolated are administered in a manner that physically isolates them from the recipient's immune system. Examples of immunological isolation methods include, but are not limited to, well known technologies and devices such as microencapsulation, biocompatible matrices, diffusion chambers, implantable cartridges, implant devices with membrane assemblies and other containers with membranes. It is preferred that cells are immunologically isolated by maintaining them in the body within an implant device.

The term "isolated nucleic acid" should be construed to refer to a nucleic acid sequence, or segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

As used herein, "an isolated nucleic acid molecule" may be one which either is not present in stromal cells or is not expressed as a protein in sufficiently high levels in stromal cells until it is introduced into the cell by means such as, but not limited to, classical transfection (calcium phosphate or DEAE dextran-mediated transfection), electroporation, microinjection, liposome-mediated transfer, chemical-mediated transfer, ligand mediated transfer or recombinant viral vector transfer.

As used herein, "gene construct" is meant to refer to an isolated nucleic acid molecule which includes coding sequences that encode a beneficial protein operably linked to a promoter/regulatory sequence having elements sufficient for expression of the coding sequence in stromal cells.

As used herein, "promoter/regulatory sequence" means a DNA sequence which is required for specific expression of a gene operably linked to the promoter/regulator sequence. In some instances, this sequence may be the core promoter sequence and in other instances, this sequence may also include an enhancer sequence and other regulatory elements which are required for expression of the gene in a tissue-specific or otherwise inducible or constitutive manner.

By describing two nucleic acid sequences as "operably linked" as used herein, is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

As used herein, "heterologous gene" is meant to refer to the coding sequence of the gene construct.

A "heterologous protein" as used herein, is one which is encoded by a heterologous gene.

As used herein, the terms "recombinant genetic material" and "recombinant gene" are used interchangeably and meant to refer to genomic DNA, cDNA, synthetic DNA and RNA, mRNA and antisense DNA and RNA which is introduced into the stromal cell. The recombinant genetic material may be heterologous genetic material or may be an additional copy or copies of genetic material normally found in the individual or animal. When cells are used as a component of a pharmaceutical composition in a method for treating a human disease, disorder or condition, the recombinant genetic material that is used to transform the cells may encode a protein selected as a therapeutic used to treat the individual and/or to render the cells more amenable to transplantation.

As used herein, "transfected stromal cells" is meant to refer to stromal cells to which a gene construct has been provided using any technology used to introduce nucleic acid molecules into cells such as, but not limited to, classical transfection (calcium phosphate or DEAE dextran mediated transfection), electroporation, microinjection, liposome-mediated transfer, chemical-mediated transfer, ligand mediated transfer or recombinant viral vector transfer.

As used herein, the term "pre-differentiated" should be construed to mean isolated stromal cells which are cocultured with a substantially homogeneous population of differentiate cells such that the isolated stromal cells differentiate and acquire phenotypic characteristics of the differentiated cells.

As used herein, the term "phenotypic characteristics" should be construed to mean at least one of the following characteristics: morphological appearance, the expression of a specific protein, a staining pattern, and the ability to be stained with a substance.

The phrase "substantially homogeneous population of differentiated cells" as used herein should be construed to mean a population of cells wherein at least 75% of the cells exhibit the same differentiated phenotype.

The phrase "directing differentiation" as used herein, should be construed to mean the induction of a differentiated phenotype in an undifferentiated cell by coculturing the undifferentiated cell in the presence of a substantially homogeneous population of differentiated cells.

Description

The present invention is based on the discovery that MSCs which are isolated by adhesion to plastic and are infused into mammal brain, engraft, migrate, and differentiate into cells of the central nervous system, while other cells remain as precursor cells which throw off daughter cells that differentiate into cells of the central nervous system. This discovery allows for the successful treatment of an individual, i.e., a mammal and preferably, a human patient, suffering from a disease, disorder or a condition associated with the central nervous system, by either providing the individual with stromal cells obtained from a normal, matched syngeneic donor, or by isolating stromal cells from the individual, culturing the cells and genetically modifying them to correct whatever genetic defect is responsible for the disease, disorder or condition associated with the defect in the central nervous system.

In a preferred embodiment of the invention, stromal cells obtained from a matched donor are administered to an individual suffering from a disease, disorder or condition involving the central nervous system, in order to augment or replace the diseased and damaged nervous cells. Stromal cells are preferably administered to a human. Stromal cells are further preferably administered to the brain of the human. In some instances, the cells are administered to the corpus striatum portion of the human brain. The precise site of administration of the stromal cells will depend on any number of factors, including but not limited to, the site of the lesion to be treated, the type of disease being treated, the age of the human and the severity of the disease, and the like. Determination of the site of administration is well within the skill of the artisan versed in the administration of such cells.

The mode of administration of the stromal cells to the central nervous system of the human may vary depending on several factors including the type of disease being treated, the age of the human, whether the stromal cells are differentiated or not, whether the stromal calls have heterologous DNA introduced therein, and the like. An example of administration of stromal cells directly into brain tissue is provided herein in the experimental details section. In that example, cells are introduced into the brain of a mammal be first creating a hole in the cranium through which the cells are then passed into the brain tissue. Cells may be introduced by direct injection, by using a shunt, or by any other means used in the art for the introduction of compounds into the central nervous system.

There are several ways in which stromal cells may be used in a mammal, preferably, a human, to treat diseases of the central nervous system. For example, stromal cells may be used as precursor cells that differentiate following introduction the central nervous system or as cells which have been differentiated into neural cells prior to introduction into the central nervous system. In either situation, as the data presented herein establishes, the cells become permanent residents of the central nervous system. These cells may therefore replace cells in the central nervous system which have been lost as a result of a genetic disease, trauma, or other injury. In addition, prior to introduction into the central nervous system, stromal cells may be genetically engineered to produce molecules such as cytokines, neurotrophins, and the like, which will beneficially influence cells which are already present in the central nervous system. For example, genetically engineered stromal cells which are then introduced into the central nervous system may be used to repair any central nrevous system damage, and/or to combat tumors of the central nervous system.

The data presented herein establish that human stromal cells which are cocultured with rat astrocytes become positive for glial fibrillary acidic protein, a marker for early astrocytes. In other words, it is possible to direct the differentiation of stromal cells by coculture of stromal cells with a desired cell type. Thus, it is possible, according to the data presented herein, to pre-differentiate isolated stromal cells to evolve into a desired phenotype prior to their introduction into the central nervous tissue. It is further possible that isolated stromal cells which are introduced into the central nervous system can differentiate in brain tissue or in spinal cord tissue into oligodendrocytes, Schwan cells and neurons.

Based on these considerations, the types of diseases which are treatable using isolated stromal cells which are introduced directly into the central nervous system are many. For example, among neonates and children, the cells may be used for treatment of a number of genetic diseases of the central nervous system, including, but not limited to, Tay-Sachs disease and he related Sandhoff's disease, Hurler's syndrome and related mucopolysaccharidoses and Krabbe's disease. To varying extents, these diseases also produce lesions in the spinal cord and peripheral nerves and they also have non-neurological effects. While the non-neurological effects of these diseases may be treatable by bone marrow transplantation, the central nervous system effects do not improve despite bone marrow transplantation. The method of the present invention may therefore be used to address the central nervous system effects of these types of diseases. In addition, in neonates and children, treatment of head trauma during birth or following birth is treatable by introducing stromal cells directly into the central nervous system of the children. Central nervous system tumor formation in children is also treatable using the methods of the present invention.

With respect to adult diseases of the central nervous system, isolated stromal cells are useful for treatment of Parkinson's disease, Alzheimer's disease, spinal cord injury, stroke, trauma, tumors, degenerative diseases of the spinal cord such as amyotropic lateral sclerosis, Huntington's disease and epilepsy. Treatment of multiple sclerosis may also be possible.

Treatment of spinal cord injuries is possible using the method of the present invention. Some prior art methods of treating spinal cord injuries involve using fibroblast cells to deliver of neurotrophins to the site of spinal cord lesions in animals. The neurotrophins delivered in this manner serve to reduce the lesion or otherwise treat the injury. However, unlike stromal cells, fibroblasts continue to produce large amounts of collagen which causes fibrosis at the site of the lesion, thereby negating the beneficial effects of the treatment. Thus, delivery of neurotrophins to spinal cord lesions using genetically engineered stromal cells has significant advantages over prior art methods because stromal cells do not produce large amounts of collagen and therefore will not cause fibrosis.

Although the data presented herein establish that the direct introduction of stromal cells into the central nervous system is useful for treatment of diseases of the central nervous system, in certain instances, isolated stromal cells may also be useful for treatment of diseases or injury associated with the eye. Stromal cells, when injected directly into the eye may differentiate into retinal pigmented epithelium, i.e., the cells that line the posterior surface of the retina and that appear to serve as nutrient cells for cones and rods in the eye. Alternatively, it may be possible to pre-differentiate isolated stromal cells into retinal pigmented epithelium by coculturing stromal cells with cells of the eye. That stem cells give rise to cells of the eye has been observed in fish. Fish eyes continue to grow throughout the life of the fish. In that instance, there are stem cells in the anterior edges of the eye that differentiate into both retinal pigmented epithelium and the light sensitive cells of the retina. Isolated stromal cells may be used to treat a variety of degenerative diseases of the eye, including degenerative diseases of the optic nerve retinal pigmented epithelial cells. The diseases include, but are not limited to, macular degeneration, a process of unknown origin which leads to a central visual loss in the elderly. Also included is blindness resulting from diabetes or arterial sclerosis, i.e., diseases of the eye which are the result of lesions in the vascular supply of the retina. In addition, rare diseases such as, for example, Laber's congenital amaurosis, may also be treatable using the methods of the invention.

In some aspects of the invention, an individual suffering from a disease, disorder, or a condition that affects the central nervous system and that is characterized by a genetic defect may be treated by supplementing, augmenting and/or replacing defective or deficient neurological cells with cells that correctly express a normal neurological cell gene. The cells which are to be introduced into the individual may be derived from stromal cells obtained from a normal matched donor or they may be stromal cells obtained from the individual to be treated. The cells may also be genetically modified to correct the defect. But this is not the only instance where the cells can be genetically modified.

In another embodiment of the invention, an individual suffering from a disease, disorder or a condition that affects the central nervous system and that is characterized by a genetic defect can be treated by supplementing, augmenting and/or replacing defective cells with cells that correctly express a normal gene. The cells may be derived from stromal cells obtained from a normal matched donor or stromal cells obtained from the individual to be treated. The cells may also be genetically modified to correct the defect.

An example of a disease, disorder or a condition that affects the central nervous system and that is characterized by a genetic defect is a brain tumor. An individual suffering from a brain tumor may be administered stromal cells obtained from a normal matched donor, which stromal cells differentiate into normal brain cells that may be used to replace or supplement the brain cells in the individual which has the tumor cells. The normal cells will compensate for the defective cells in the brain.

In an alternative embodiment, stromal cells are isolated from an individual suffering from a brain tumor and a gene capable of killing or otherwise arresting the replication of the tumor cells is inserted into the isolated stromal cells. The transfected cells are then reintroduced into the individual. The growth and/or replication of the tumor cells is arrested and/or apoptosis of the tumor cells is induced.

In one aspect of the invention, an individual suffering from a disease, disorder or a condition of the central nervous system can be treated as follows. Isolated stromal cells are obtained, they are expanded and are systemically administered to the individual. Some of the isolated/expanded stromal cells will develop into normal brain cells. Normal stromal cells expand more quickly than defective stromal cells and the expanded rejuvenated population will reflect a greater proportion of normal cells. Thus, repopulation of the central nervous system tissue with an expanded and rejuvenated population of stromal cells serves to provide a population of normal central nervous system cells which facilitate correction of the defect in the central nervous system tissue. Also, stromal cells may be pre-differentiated into, for example, astrocytes, by following the protocols provided herein, prior to administration of the stromal cells to the central nervous system.

In addition to replacing defective cells with repaired cells or normal cells from matched donors, the method of the invention may also be used to facilitate expression of a desired protein that when secreted in the central nervous system, has a beneficial effect. That is, stromal cells may be isolated, furnished with a gene encoding a desired protein and introduced into the central nervous system tissue of an individual. Expression of the desired protein in the central nervous system of the individual exerts a therapeutic effect in the individual. This aspect of the invention relates to gene therapy in which therapeutic proteins are administered to an individual.

According to some aspects of the present invention, immunologically isolated transfected stromal cells may be used as cell therapeutics to treat a disease, disorder or a condition characterized by a gene defect and/or a disease, disorder or a condition which can be treated using a recombinant protein in a gene therapy approach. In particular, a gene construct that comprises a heterologous gene which encodes a beneficial protein is introduced into stromal cells. The transfected stromal cells are then immunologically isolated and implanted into an individual who will benefit when the protein is expressed and secreted by the cell into the tissue of the central nervous system, preferably the brain.

Immunologically isolated stromal cells are particularly useful in cell therapeutic compositions, because in addition to being suitable hosts for expressing heterologous genes and producing heterologous proteins, stromal cells perform favorably when they are immunologically isolated. Immunologically isolated stromal cells have a very high viability when implanted in locations that lack a direct vascular blood supply. Moreover, stromal cells can be easily and readily obtained, they rapidly expand in culture making them a good source of an adequate supply of useful cells for immunologically isolated cell therapeutics.

According to the present invention, gene constructs which comprise nucleotide sequences that encode heterologous proteins are introduced into stromal cells. That is, the cells are genetically altered to introduce a gene whose expression has therapeutic effect on the individual. According to some aspects of the invention, stromal cells obtained from the same individual to be treated or from another individual, or from a non-human animal, may be genetically altered to replace a defective gene and/or to introduce a gene whose expression has therapeutic effect on the individual.

Further, according to the present invention, stromal cells are useful to prepare transfected cells that can be immunologically isolated and express heterologous beneficial proteins thereby providing a means to correct genetic defects and/or to produce therapeutic proteins in the individual. Stromal cells may be isolated with relative ease and isolated stromal cells may be cultured to increase the number of cells available. Stromal cells can be transfected, immunologically isolated and implanted with a high degree of viability into locations that lack direct blood supply such as subcutaneous locations.

In some embodiments, stromal cells may be immortalized, such as by using SV40 virus, a retrovirus, an adenovirus or other transforming virus, or by using proteins having transforming properties. In some aspects of the invention, an individual suffering from a disease, disorder or a condition may be treated by supplementing, augmenting and/or replacing defective or deficient genes by providing immunologically isolated stromal cells containing gene constructs that include normal, functioning copies of the deficient gene. This aspect of the invention relates to gene therapy in which the individual is provided with genes for which they are deficient in presence and/or function. The gene provided by the cell compensates for the defective gene of the individual, because, when the gene is expressed in the central nervous system tissue, a protein is produced which serves to alleviate or otherwise treat the disease, disorder or condition in the individual. Such genes preferably encode proteins that are secreted.

The stromal cells are transfected and are administered to the central nervous system of the individual "as is" or in an immunologically isolated form. In some embodiments, stromal cells are transfected with genes for which the individual to be treated suffers from a complete absence of a nonmutated copy of the gene, or suffers from an absence or insufficient expression of a nonmutated form of the protein. Stromal cells are transfected with a non-mutated copy of the gene in an expressible form. That is, the protein encoded by the transfected gene will be expressed by the stromal cells, preferably as a secreted protein.

In addition to replacing defective genes with functional genes, the invention may also be used to express desired secreted proteins which exert a biologically active therapeutic or prophylactic effect. Such proteins are preferably secreted by the cells. That is, stromal cells may be isolated, furnished with a gene encoding a desired protein, they may then be administered to the individual as is, or in an immunologically isolated form, and the desired protein is expressed therein. According to this aspect of the invention, the isolated stromal cells serve as vectors for introducing therapeutic genes into the individual as well as hosts for such genes when the cells are administered to the individual.

In such embodiments, stromal cells are transfected with genes that encode proteins which have a therapeutic effect when expressed in the individual to be treated. Rather than administering the therapeutic protein directly to the individual which may require repeated administrations, the present invention provides a means of administering a therapeutic protein to the individual in a continuous manner by administering to the individual cells which produce the protein. Stromal cells are transfected with a gene that encodes the protein in an expressible form. That is, the protein encoded by the transfected gene will be expressed in the stromal cells, preferably as a secreted protein. Thus, the invention includes a method of treating a disease, disorder or condition of the central nervous system wherein stromal cells that are transfected with genes that encode a protein are administered to the individual. The protein is expressed and has a therapeutic effect. Examples of therapeutic proteins include, but are not limited to cytokines, chemokines, neurotrophins, and the like.

In all cases in which a gene construct is transfected into a stromal cell, the heterologous gene is operably linked to an appropriate promoter/regulatory sequence which is required to achieve expression of the gene in the stromal cell. Such promoter/regulatory sequences include but are not limited to, constitutive and inducible and/or tissue specific and differentiation specific promoters. Constitutive promoters include, but are not limited to, the cytomegalovirus immediate early promoter and the Rous sarcoma virus promoter. In addition, housekeeping promoters such as those which regulate expression of housekeeping genes may also be used. Other promoters include those which are preferentially expressed in cells of the central nervous system, such as, but not limited the promoter for the gene encoding glial fibrillary acidic protein. In addition, promoter/regulatory elements may be selected such that gene expression is inducible. For example, a tetracycline inducible promoter may be used (Freundlich et al., 1997, Meth. Enzymol. 283:159–173).

The gene construct is preferably provided as an expression vector which includes the coding sequence of a heterologous protein operably linked to essential promoter/regulatory sequences such that when the vector is transfected into the cell, the coding sequence is expressed by the cell. The coding sequence is operably linked to the promoter/regulatory elements necessary for expression of the sequence in the cells. The nucleotide sequence that encodes the protein may be cDNA, genomic DNA, synthesized DNA or a hybrid thereof or an RNA molecule such as mRNA.

The gene construct, which includes the nucleotide sequence encoding the beneficial protein operably linked to the promoter/regulatory elements, may remain present in the cell as a functioning episomal molecule or it may integrate into the chromosomal DNA of the cell. Genetic material may be introduced into cells where it remains as separate genetic material in the form of a plasmid. Alternatively, linear DNA which can integrate into a host cell chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The elements in the promoter/regulatory sequences that are necessary for gene expression include: a promoter, an initiation codon, a stop codon, and a polyadenylation signal. It is necessary that these elements be operable in the stromal cells or in cells that arise from the stromal cells after infusion of the cells into an individual. Moreover, it is necessary that these elements be operably linked to the nucleotide sequence that encodes a protein such that the nucleotide sequence can be expressed in the stromal cells and thus the protein can be produced. Initiation codons and stop codon are generally considered to be part of a nucleotide sequence that encodes the protein. However, it is necessary that these elements are functional in the stromal cells or cells that arise from stromal cells. Similarly, the promoters and polyadenylation signals used must be functional within the stromal cells or cells that arise from stromal cells.

Examples of promoter/regulatory sequences useful to practice the present invention include but are not limited to promoter/regulatory sequences that are active in many cells such as the cytomegalovirus promoter, the SV40 promoter and many retroviral promoters. Other examples of promoter/regulatory sequences useful to practice the present invention include but are not limited to tissue-specific promoter/regulatory sequences,. i.e. promoter/regulatory sequences that function in some tissues but not in others; also, promoter/regulatory sequences of genes normally expressed in stromal cells with or without specific or general enhancer sequences. In some embodiments, promoter/regulatory sequences are used which constitutively express genes in stromal cells with or without enhancer sequences. Enhancer sequences are provided in some embodiments when appropriate or desirable.

Examples of polyadenylation signals useful to practice the present invention include but are not limited to the human collagen I polyadenylation signal, the human collagen II polyadenylation signal, and the SV40 polyadenylation signal.

In order for genetic material in an expression vector to be expressed, the promoter/regulatory elements must be operably linked to the nucleotide sequence that encodes the protein. In order to maximize protein production, promoter/regulatory sequences may be selected which are well suited for gene expression in the desired cells. Moreover, codons may be selected which are most efficiently transcribed in the cell. One having ordinary skill in the art can produce recombinant genetic material as expression vectors which are functional in the desired cells.

It is also contemplated that promoter/regulatory elements may be selected to facilitate tissue specific expression of the protein. Thus, for example, specific promoter/regulatory sequences may be provided such that the heterologous gene will only be expressed in the tissue where the immunologically isolated stromal cells are implanted. In addition, promoter/regulatory elements may be selected such that gene expression is inducible. For example, a tetracycline inducible promoter may be used (Freundlich et al., 1997, Meth. Enzymol. 283:159–173).

The heterologous protein preferably includes a signal sequence which directs the transport and secretion of the heterologous protein in the stromal cell. The signal sequence is generally processed and removed upon secretion of the mature protein from the cell.

In addition to providing cells with recombinant genetic material that either corrects a genetic defect in the cells, that encodes a protein which is otherwise not present in sufficient quantities and/or functional condition so that the genetic material corrects a genetic defect in the individual, and/or that encodes a protein which is useful as a therapeutic in the treatment or prevention of a particular disease, disorder or condition associated therewith, genetic material may also be introduced into the stromal cells used in the present invention to provide a means for selectively terminating such cells should such termination become desirable. Such means for targeting cells for destruction may be introduced into stromal cells which are to be otherwise genetically modified as well as those to which no other recombinant genetic material is to be introduced.

According to the invention, isolated stromal cells are furnished with genetic material which renders them specifically susceptible to destruction. For example, stromal cells may be provided with a gene that encodes a receptor that can be specifically targeted with a cytotoxic agent. An expressible form of a gene that can be used to induce selective cell death can be introduced into the cells. In such a system, cells expressing the protein encoded by the gene are susceptible to targeted killing under specific conditions or in, the presence or absence of specific agents. For example, an expressible form of a herpes virus thymidine kinase (herpes tk) gene can be introduced into the cells and used to induce selective cell death. When the introduced genetic material that includes the herpes tk gene is introduced into the individual, herpes tk will be produced. If it is desirable or necessary to kill the implanted cells, the drug gangcyclovir can be administered to the individual which will cause the selective killing of any cell producing herpes tk. Thus, a system can be provided which allows for the selective destruction of implanted cells.

Stromal cells may be obtained by removing bone marrow cells from a donor and placing the cells in a sterile container with a plastic surface or other appropriate surface that the cells come into contact with. The stromal cells will adhere to the plastic surface within 30 minutes to about 3 days. After at least 30 minutes, preferably about four hours, the non-adhered cells may be removed and discarded. The adhered cells are stromal cells which are initially non-dividing. However, after about 2–4 days, the cells begin to proliferate and can be cultured to increase their numbers using standard cell culture techniques.

According to preferred embodiments, stromal cells are cultured in medium supplemented with 2–20% fetal calf serum or serum-free medium with or without additional supplements. Isolated stromal cells may be transfected using well known techniques readily available to those having ordinary skill in the art. Foreign genes may be introduced into stromal cells using standard methods which are employed for introducing a gene construct into cells which express the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA having a desired sequence into the stromal cell. In some embodiments, recombinant retrovirus vectors are used to introduce DNA having a desired sequence into the stromal cell. In some embodiments, standard calcium phosphate, DEAE dextran or lipid carrier mediated transfection techniques are employed to incorporate a desired DNA into dividing cells. Standard antibiotic resistance selection techniques can be used to identify and select transfected cells. In some embodiments, DNA is introduced directly into cells by microinjection. Similarly, well known electroporation or particle bombardment techniques can be used to introduce foreign DNA into isolated stromal cells. A second gene is usually co-transfected or linked to the therapeutic gene. The second gene is frequently a selectable antibiotic-resistance gene. Transfected cells can be selected by growing the cells in an antibiotic that kills cells that do not take up the selectable gene. In most cases where the two genes are unlinked and co-transfected, the cells that survive the antibiotic treatment contain and express both genes.

After isolating the stromal cells, the cells can be administered to the human upon isolation or following a period of in vitro culture. Isolated stromal cells may be administered upon isolation, or may be administered within about one hour after isolation. Generally, stromal cells may be administered immediately upon isolation in situations in which the donor is large and the recipient is an infant. It is preferred that stromal cells are cultured prior to administration. Isolated stromal cells can be cultured from 1 hour to up to over a year. In some preferred embodiments, the isolated stromal are cultured prior to administration for a period of time sufficient to allow them to convert from non-cycling to replicating cells. In some embodiments, the isolated stromal cells are cultured for 3–30 days, preferably, 5–14 days, more preferably, 7–10 days. In other embodiments, the isolated stromal cells are cultured for 4 weeks to a year, preferably, 6 weeks to 10 months, more preferably, 3–6 months.

In other embodiments, the isolated stromal cells are cocultured so that they differentiate into astrocytes or other neural cells prior to administration of the central nervous system.

If the cells are to be transfected, either isolated, non-cycling stromal cells are first transfected and then are administered as non-cycling cells; isolated, non-cycling stromal cells are first transfected, then cultured for a period of time sufficient to convert them from non-cycling to replicating cells and then are administered; isolated, non-cycling stromal cells are first cultured for a period of time sufficient to convert them from non-cycling to replicating cells, they are then transfected, and then are administered; or isolated, non-cycling stromal cells are first cultured for a period of time sufficient to convert them from non-cycling to replicating cells, they are then transfected, they are then cultured and then administered to the human. In some embodiments, stromal cells are isolated, transfected and immediately administered to the human.

It is preferred that stromal cells are cultured prior to transfection and/or administration. Isolated stromal cells can be cultured from cultured for 3–30 days, in some embodiments, 5–14 days, in other embodiments, 7–10 days prior to transfection. Transfected stromal cells can be cultured for 3–30 days, in some embodiments, 5–14 days, in some embodiments, 7–10 days prior to administration. Isolated stromal cells can be cultured from 3–30 days, in some embodiments, 5–14 days, in some embodiments, 7–10 days prior to transfection, and upon transfection, additionally cultured for 3–30 days, in some embodiments, 5–14 days, in some embodiments, 7–10 days prior to administration. In some embodiments, the isolated stromal cells are cultured for 4 weeks to a year, in some embodiments, 6 weeks to 10 months, in some embodiments, 3–6 months prior to transfection. Transfected stromal cells can be cultured for 4 weeks to a year, in some embodiments, 6 weeks to 10 months, in some embodiments, 3–6 months prior to administration. In some embodiments, the isolated stromal cells are cultured for 4 weeks to a year, in some embodiments, 6 weeks to 10 months, in some embodiments, 3–6 months prior to transfection and upon transfection, further cultured for 4 weeks to a year, in some embodiments, 6 weeks to 10 months, in some embodiments, 3–6 months prior to administration.

For administration of stromal cells to the human, the isolated stromal cells are removed from culture dishes, washed with saline, centrifuged to a pellet and resuspended in a glucose solution which is infused into the patient. In some embodiments, bone marrow ablation is undertaken prior to infusion in order to make space in the bone for introduced cells. Bone marrow ablation may be accomplished by X-radiating the individual to be treated, administering drugs such as cyclophosphamide or by a combination of X-radiation and drug administration. In some embodiments, bone marrow ablation is produced by administration of radioisotopes known to kill metastatic bone cells such as, for example, radioactive strontium, $^{135}$Samarium or $^{166}$Holmium (see Applebaum et al., 1992, Blood 80(6):1608–1613).

If bone marrow ablation precedes administration of stromal cells, the administration of stromal cells must be accompanied by the administration of non-adherent cells which comprise blood cell precursors necessary for survival. Such non-adherent cells may be saved from the same sample used as starting materials in the isolation of stromal cells and stored or they can be derived from a different sample. In some preferred embodiments, the non-adherent cells are provided by the recipient/patient. Prior to procedures which generate bone marrow ablation, a sample of the patient/recipients bone marrow is obtained and stored. The entire sample may be used or the non-adherent cells may be isolated and used to administer in conjunction with isolated stromal cells. Non-adherent cells administered in conjunction with administration of stromal cells may be administered separately before or after stromal cell administration or may be mixed with isolated stromal cells prior to administration.

In some embodiments, isolated stromal cells are administered to the brain by direct infusion as described herein in the experimental examples section. In other embodiments, isolated stromal cells are administered to the central nervous system, i.e., the spinal cord, by simple injection, etc.

Between about $10^5$ and about $10^{13}$ cells per 100 kg person are administered per infusion. In some embodiments, between about $1.5 \times 10^6$ and about $1.5 \times 10^{12}$ cells are infused intravenously per 100 kg person. In some embodiments, between about $1 \times 10^9$ and about $5 \times 10^{11}$ cells are infused intravenously per 100 kg person. In some embodiments, between about $4 \times 10^9$ and about $2 \times 10^{11}$ cells are infused per 100 kg person. In some embodiments, between about $5 \times 10^8$ cells and about $1 \times 10^1$ cells are infused per 100 kg person.

In some embodiments, a single administration of cells is provided. In some embodiments, multiple administrations are provided. In some embodiments, multiple administrations are provided over the course of 3–7 consecutive days. In some embodiments, 3–7 administrations are provided over the course of 3–7 consecutive days. In some embodiments, 5 administrations are provided over the course of 5 consecutive days.

In some embodiments, a single administration of between about $10^5$ and about $10^{13}$ cells per 100 kg person is provided. In some embodiments, a single administration of between about $1.5 \times 10^8$ and about $1.5 \times 10^{12}$ cells per 100 kg person is provided. In some embodiments, a single administration of between about $1 \times 10^9$ and about $5 \times 10^{11}$ cells per 100 kg person is provided. In some embodiments, a single administration of about $5 \times 10^{10}$ cells per 100 kg person is provided. In some embodiments, a single administration of $1 \times 10^{10}$ cells per 100 kg person is provided.

In some embodiments, multiple administrations of between about $10^5$ and about $10^{13}$ cells per 100 kg person are provided. In some embodiments, multiple administrations of between about $1.5 \times 10^8$ and about $1.5 \times 10^{12}$ cells per 100 kg person are provided. In some embodiments, multiple administrations of between about $1 \times 10^9$ and about $5 \times 10^{11}$ cells per 100 kg person are provided over the course of 3–7 consecutive days. In some embodiments, multiple administrations of about $4 \times 10^9$ cells per 100 kg person are provided over the course of 3–7 consecutive days. In some embodiments, multiple administrations of about $2 \times 10^{11}$ cells per 100 kg person are provided over the course of 3–7 consecutive days. In some embodiments, 5 administrations of about $3.5 \times 10^9$ cells are provided over the course of 5 consecutive days. In some embodiments, 5 administrations of about $4 \times 10^9$ cells are provided over the course of 5 consecutive days. In some embodiments, 5 administrations of about $1.3 \times 10^{11}$ cells are provided over the course of 5 consecutive days. In some embodiments, 5 administrations of about $2 \times 10^{11}$ cells are provided over the course of 5 consecutive days.

Stromal cells in diffusion chambers are described in Benayahu et al., 1989, J. Cell Physiol. 140:1–7; Mardon et al., 1987, Cell Tissue Res. 250:157–165. After introducing the gene construct into the stromal cells, the cells can be immunologically isolated immediately or following a period of in vitro culture. Stromal cells can be implanted after they are immunologically isolated. Stromal cells may be immunologically isolated using any number of well known methods using readily available starting materials and/or devices. Stromal cells may be microencapsulated using many such microencapsulation protocols including those disclosed, for example, in U.S. Pat. Nos. 4,391,909, 4,806,355, 4,942,129, and 5,334,640.

Stromal cells may be administered to an individual in chambers using diffusible membranes or they may be encapsulated in microbeads. In another embodiment, the stromal cells are contained in hollow fibers such as those available from Amicon, Inc. (Beverly Mass.). These fibers are used for example to make cartridges for dialysis. One end can be pulled out from under the skin and reduced in size if dosages of the protein made by the cells are to be reduced. The surface area of the fibers is very high. Further, cells in the fiber can be flushed out and replaced periodically. Hollow fibers are described on pages 50–51 of Amicon, Inc. Publication No. 323.

Similarly, incorporation of transfected stromal cells in biocompatible matrices facilitates secretion of a beneficial protein to the individual while maintaining the cells in an immunologically isolated condition. Examples of biocompatible matrices are disclosed, for example, in U.S. Pat. Nos. 4,902,295 and 4,997,443. In some embodiments, transfected stromal cells are immunologically isolated by encasing them within tissue implant systems that are membrane assemblies. That is, cells are maintained in containers that include at least one porous membrane. The cells within the membrane assembly are immunologically isolated while beneficial proteins may be made available to the individuals by passing through the membrane. Implant devices which are membrane assemblies, include, but are not limited to, those described in U.S. Pat. Nos. 5,314,471 and 5,344,454.

According to one embodiment of the invention, an implant device is provided which comprises two ten ring assembles. Each ring assembly comprises a circular plastic ring and a 0.3 micron millipore membrane covering the area of the circle. Transfected stromal cells are disposed between the two ring assembly which are connected to each other at the circumference. The constructed implant device is preferably implanted subcutaneously.

In some preferred implant devices, about $10^5$ to about $10^{13}$ cells are provided. Preferred ranges of cells to be administered when immunologically isolated are as described herein when the cells are not immunologically isolated. Immunologically isolated cells may be implanted into the ventricles of the subdural space, or into the subarachnoid space of the brain and spinal column.

It is preferred that stromal cells are cultured prior to immunological isolation. Stromal cells can be cultured from 1 hour to over a year. In some preferred embodiments, the stromal cells are cultured for a period of time sufficient to allow them to convert from non-cycling to replicating cells. In some embodiments, the stromal cells are cultured for 3–30 days, preferably 5–14 days, more preferably 7–10 days. In some embodiments, the stromal cells are cultured for 4 weeks to a year, preferably 6 weeks to 10 months, more preferably 3–6 months. In preferred embodiments, cells are either isolated, non-cycling stromal cells that are first transfected and then immunologically isolated, then implanted as noncycling cells; isolated, non-cycling stromal cells that are first transfected, then cultured for a period of time sufficient to convert from non-cycling to replicating cells, then immunologically isolated and then implanted; isolated, non-cycling stromal cells that are first cultured for a period of time sufficient to convert from non-cycling to replicating cells, then transfected, then immunologically isolated and then implanted; or isolated, non-cycling stromal cells that are first cultured for a period of time sufficient to convert from non-cycling to replicating cells, then transfected, then cultured, then immunologically isolated and then implanted. In some embodiments, stromal cells are isolated, transfected, immunologically isolated and implanted. It is preferred that stromal cells are cultured prior to and after transfection, prior to immunological isolation. Isolated stromal cells can be cultured from 3–30 days, in some embodiments, 5–14 days, in some embodiments, 7–10 days prior to transfection. Transfected stromal cells can be cultured from 3–30 days, in some embodiments, 5–14 days, in some embodiments, 7–10 days prior to administration. Isolated stromal cells can be cultured from 3–30 days, in some embodiments, 5–14 days, in some embodiments, 7–10 days prior to transfection and upon transfection, additionally cultured for 3–30 days, in some embodiments, 5–14 days, in some embodiments, 7–10 days prior to administration. In some embodiments, the isolated stromal cells are cultured for 4 weeks to a year, in some embodiments, 6 weeks to 10 months, in some embodiments, 3–6 months prior to transfection. Transfected stromal cells can be cultured for 4 weeks to a year, in some embodiments, 6 weeks to 10 months, in some embodiments, 3–6 months prior to implantation.

The invention will be further described by reference to the following experimental examples. These examples are provided for the purposes of illustration only and are not intended to be limiting unless otherwise specified. Thus, the invention shall in no way be construed as being limited to the following examples, but rather, shall be construed to encompass any and all variations which become evident as a result of the teaching provided herein.

EXAMPLES

Example 1

Stromal Cells as Precursor Cells of Connective Tissues

Cells from a transgenic mouse line that expresses a human mini-gene for collagen I in a tissue-specific manner were used to determine whether precursor mesenchymal cells from marrow that are expanded in culture can serve as long-term precursors of bone and other connective tissues after intravenous infusion into irradiated mice. The marker gene consisted of an internally deleted mini-gene encoding the human proα1 (I) chain of procollagen I that causes synthesis of shortened proα1 (I) chains (Khillan et al., 1991, J. Biol. Chem. 266:23373–23379; Pereira et al., 1983, J. Clin. Invest. 91:709–716; and Sokolov et al., 1993, Biochemistry 32:9242–9249). Cells expressing the gene were obtained from a line of transgenic mice in which the copy number of the human mini-gene relative to the endogenous mouse gene was about 100 to 1, and the steady-state levels of mRNA expressed by the human mini-gene relative to mRNA expressed by the endogenous mouse gene was about 0.5:1 in most tissues.

Donor cells obtained from marrow partially enriched for mesenchymal precursors were prepared using standard protocols (Friedenstein et al., 1976, Exp. Hemat. 4:267–274; Castro-Malaspina et al., 1980, Blood 56:289–301; Piersma et al., 1985, Exp. Hematol 13:237–243; Simmons et al., 1991, Blood 78:55–62; Beresford et al., 1992, J. Cell. Sci.102:341–351; Liesveld et al., 1989, Blood 73:1794–1800; Liesveld et al., 1990, Exp. Hematot. 19:63–70; Bennett et al., 1991, J. Cell. Sci. 99:131–139). Briefly, the ends of long bones from the transgenic mice were cut, and the marrow was extracted with a pressurized syringe filled with α-MEM (Sigma) containing 10% fetal bovine serum (Atlanta Biologicals). About $10^7$ nucleated cells were plated onto 175 cm$^2$ plastic culture flasks in 25 ml of α-MEM containing 10% fetal bovine serum. After 4 hours, the non-adherent cells were discarded by replacing the medium. Foci containing two to four fibroblast-like cells appeared in 2 to 3 days, and the foci grew to near-confluent colonies in about 1 week. The yield was about $10^7$ cells per flask after trypsin digestion. Most of the cells were fibroblast-like, but a few macrophages and adipocytes were also seen when the cells were examined under phase contrast microscopy.

About $10^5$ of the cultured adherent cells were mixed with $6 \times 10^5$ non-adherent cells obtained by incubation of marrow from normal mice for 4 hours on 175 cm$^2$ flasks under the same conditions used for the initial isolation of the adherent cells. The mixture of about $7 \times 10^5$ cells in 0.2 to 0.4 ml of α-MEM and 10% fetal bovine serum was injected into the tail vein of each recipient mouse.

Eight-week old mice from the same inbred FVB/N line were prepared to receive the donor cells by irradiation with a $^{137}$Cu irradiator (Atomic Energy of Canada, Ltd.). The unit had a dose rate of 116 cG/min with a parallel opposed beam configuration. Each animal received 9.0 Gy in two fractions with a 4 hour interval (4.5 Gy+4.5 Gy) (O'Hara et al., 1991, Exp. Hemat. 19:878–881). One to 2 hours after the second radiation fraction, the mixture of marked adherent cells and normal non-adherent cells was injected intravenously. Control irradiated mice that did not receive a cell infusion died after 10 to 13 days of marrow failure.

To follow the fate of the donor cells, two PCR assays for the human COL1A1 mini-gene and the mouse endogenous COL1A1 gene were developed. Using a two-primer assay, the values for the ratio of the human to mouse genes were linear over a range of $10^{-4}$ to about $10^{+1}$ and, therefore, resulted in about $10^{-6}$ to $10^{-1}$ donor cells per recipient cell. Using the three-primer assay, the values were linear over a range of about $10^{-3}$ to $10^{+2}$ and, therefore, resulted in about $10^{-5}$ to 1 donor cell per recipient call.

Assays of irradiated mice after one day indicated only trace amounts of the donor cells in marrow, spleen, bone, lung or brain (Table 1). Slightly higher levels were seen at seven days. At 30 days and 150 days, progeny of the donor cells accounted for 2.0 to 12% of the cells in marrow, spleen, bone and lung (Table 1). At 150 days, they also accounted for 1.5 to 5.0% of the cells in xiphoid cartilage that was dissected free of any mineralized or fibrous tissue under a microscope. Although the mean values appeared to show a decrease between 1 and 5 months, there was no statistically significant decrease in the combined values for marrow, spleen, bone and lung between these two time periods (Table 1). Assays of non-irradiated mice revealed only very low levels of the donor cells at the same time points (<0.0001 to 0.05%). PCR in situ assay of tissue sections of lung demonstrated that progeny of the donor cells were evenly distributed in the parenchyma of both alveoli and bronchi.

To confirm that progeny of the donor cells were present in cartilage, chondrocytes were isolated from xiphoid and articular cartilage by digestion at 37° C. overnight with 0.5 mg/ml bacterial collagenase (Sigma) in DMEM. PCR assays indicated that progeny of the donor cells accounted for 2.5% of the isolated chondrocytes.

To determine whether the donor cells became functional mesenchymal cells in the tissues they populated, tissues obtained the recipient mice were assayed by RT-PCR for expression of the human mini-gene for collagen I contained in the donor cells. In three mice assayed at 150 days, the mini-gene was expressed in bone, a tissue in which over half the protein synthesized in collagen I. The expression in bone was confirmed using a similar assay on bone cells isolated from femur and cultured for 1 week. Expression of the mini-gene for collagen I was more variable in marrow, spleen and lung, tissues in which the rate of collagen I synthesis is less than in bone. As expected, the mini-gene was not expressed in cartilage, a tissue in which about half the protein is synthesized in collagen II but in which there is no synthesis of collagen 1. The mini-gene for collagen I was also not expressed in cultures of chondrocytes obtained from the recipient mice that contained the marker gene and that synthesize collagen II but not collagen I.

The results presented herein demonstrate that after intravenous injection into irradiated mice, the expanded cultures of adherent cells efficiently populate several connective tissues. The results also demonstrate that the cells serve as true precursor cells for these tissues, since they expressed the marker gene for collagen I in a tissue-specific manner, and they were diffusely incorporated into the mesenchymal parenchyma of lung.

Example 2

Conditions for Isolation and Culture of MSCs

Conditions for culture of MSCs so that they expand but retain the stem-cell-like phenotype were examined. Table I provides data which establishes that co-culture of MSCs with pieces of bone increased the number of cells obtained after 1 week. At the same time, co-culturing with bone decreased the alkaline phosphatase (APase) levels in the cells, an observation which suggests that the cells did not differentiate into osteoblasts. Also, there was a decrease in the levels of tartrate-resistant acid phosphatase (TRAP), an observation which suggests that the cells did not differentiate into osteoclasts. Similar effects were observed with secondary cultures of the MSCs. Therefore, the results suggest that co-culturing of MSCs with pieces of bone may provide improved conditions for expansion of MSCs. Also, the medium of cultured bone pieces may be an important source of cytokines and growth factors for expansion of MSCs in culture.

In related experiments, it has been found that secondary cultures of MSCs can be maintained for long periods of time. MSCs can be passed in culture for over 4 months by trypsinization and re-plating. The cells are remarkably stable in stationary phase cultures. In one experiment, stationary cultures remained viable for over 4 months with re-feeding about once per week. In another experiment, the cells remained viable when, through an oversight, they were left in an incubator without re-feeding for 1 month.

Stable Transfection of MSCs with a Retrovirus Vector

To obtain virus for infection of MSCs, the LNCZ retroviral vector (Miller et al., 1989, BioTechniques 7:980–990) was modified so that the promoter for cytomegalovirus (pCMV) drove expression of the lacZ gene (FIG. 1). The vector was stably transfected into an amphotropic murine packaging cell line (PA317). Constitutive virus producer clones were isolated by G418 selection, and supernatant obtained from the clones was used for infection of MSCs. Primary cultures of MSCs (3 days old) were infected for three successive days with fresh supernatant obtained from the producer line with the highest titer. Staining of the cells 5 days later indicated that about 15–20% of the cells typically expressed the lacZ gene. Several cultures of the infected cells were placed under selection with G418 (0.44 $\mu$g/ml active concentration) for 5 days. Most of the cells that recovered continued to express the lacZ gene. Modifications of LNCZ were also constructed so that expression of the lacZ gene was driven by the promoter of the COL A1 gene and the promoter of the COL2 A1 gene (pCOL2A1). Expression of the lacZ gene was successfully obtained in primary cultures of MSCs using both constructs.

Replacement of Bone Cells with Normal MSCs in Transgenic Mice

MSCs obtained from normal mice were infused into transgenic mice that expressed high levels of the mutated COL1 A1 gene osteoimperfecta (OI) mice (Tables 2 and 3). One month after the infusion of normal MSCs into the mice, progeny of the donor cells accounted for 10 to 45% of the bone cells in recipient mice that had been irradiated with a maximally tolerated dose of X-ray (700 centi-Gray or cGy) Similar values were obtained in mice irradiated with one-half of the maximally tolerated dose of X-ray (350 cGy). However, reducing the dose to one-quarter (175 cGy) reduced these values in four mice to 0%, 5%, 10% and 40%. Similar results were obtained when OI transgenic mice were infused with large numbers of whole marrow cells from which MSCs were not removed (Table 3).

In five recipient mice in which the synthesis of pro$\alpha$1 (1) chains was examined (Tables 2 and 3), the replacement of the recipient's bone cells by normal donor MSCs was accompanied by an increase in the ratio of normal pro$\alpha$1 (1) chains to mutated pro$\alpha$1 (1) chains in bone. Hence, the replacement by normal cells was accompanied by the expected changes at the protein level.

Example 3

Long-term Expression of Human Genes Using hGH, Factor IX or Ob in Stably Transfected MSCs MSCs are isolated from mice and cultured under the conditions described in Pereira et al., 1995, Proc. Natl. Acad. Sci. USA 92:4857–4861, which is incorporated herein by reference. MSCs are infected with retroviral vectors or transfected with naked DNA to obtain clones that express the genes for human growth hormone (hGH), the human obesity protein (Ob), or the gene for human factor IX. Because a lacZ gene has been successfully introduced into mouse MSCs with a retroviral vector, variants of the same vector are used. At the same time, MSCs are stably transfected with electroporation (Andreason et al., 1988, BioTechniques 6:650–660; Toneguzzo et al., 1986, Mol. Call. Biol. 6:703–706), lipofectamine and nuclear injection (Mercer et al., 1992, In: Antisense Strategies, Ann. IV. Y. Acad. Sci. Biol. 660:209–218) so that larger endogenous genes can be used. Further, some of the potential disadvantages of retroviruses are avoided using alternative introduction methodology.

Standard conditions for isolation and culture are: Whole marrow is obtained from the tibias and femurs of 6- to 10-week old FVB/N mice by cutting the ends of the bones and extruding the marrow with a syringe that contains 1 to 2 ml of ice-cold α-MEM and 10% fetal bovine serum (FBS). The pooled marrow cells are dispersed by gentle shaking and counted in an automatic counter (Coulter model ZM). From $5\times10^6$ to $5\times10^7$ nucleated cells in 25 ml of α-MEM and 10% FBS are plated onto 75-$cm^2$ culture flasks. After 4 hours or 3 days, the non-adherent cells are removed by replacing the medium. The adherent cells are expanded as primary cultures for 10 to 12 days with a refeeding about every 4 days. The cells are recovered by digestion with 0.25% trypsin and 1 to 5 mM EDTA for 5 minutes at 37° C. followed by gentle scraping. The cells are diluted with α-MEM with 10% FBS and replated at a density of from $3\times10^4$ to $1\times10^5$ cells per 9.5 $cm^2$ in 6-well plates. Under these conditions, the doubling time of the cells is 19 to 22 hours. The secondary cultures are re-fed about every 4 days, and passed by trypsinization and replating under the same conditions.

Preparation of Gene Constructs

The retrovirus vector LNCX is used as the parent construct. Convenient cloning sites in the construct are used to prepare the modified constructs pRSV-lacZ, pCMV-lacZ, pCOL1/lacZ and pCOL2-lacZ (FIG. 1). The pCOL1 promoter is a 1.4 kb fragment that contains 476 bp of the promoter, the first exon and most of the first intron of the human COL1A1 gene. The promoter has been shown in transgenic mice to express a promoterless form of the COL2A1 gene in a highly tissue specific and developmental specific manner (Sokolov et al., 1995, J. Biol. Chem. 270:9622–9629). The COL2A1 promoter is a 1 kb fragment from the human COL2A1 gene (Ala-Kokko et al., 1991, J. Biol. Chem. 266:14175–14178). that confers tissue-specificity of expression (Bradham et al., 1994, J. Cell Physiol.158:61–68). The lacZ gene is replaced with the hGH gene (Nichols Laboratories); the OB gene (Considine et al., 1995, J. Clin. Invest. 95:2986–2988) or the human factor IX gene (Genetic Therapy, Inc.).

Use of the Retrovirus Vector

Retrovirus Producer Cell Lines

To establish producer cell lines, amphotrophic retrovirus packaging murine cells PA317 were used. The cells were transfected at 20% confluency in 100 mm dishes by the calcium phosphate precipitation procedure (Promega) using 15 μg of plasmid DNA that was linearized by digestion with Seal that cuts in the pBR322 region of the retrovirus vector. One day post-transfection G418 (GIBCO/BRL) was added to the medium at an active concentration of 1 mg/ml. Neomycin-resistant colonies appeared at 7 to 10 days of selection and were isolated by cloning with mechanical rings. The clones were expanded and individual clones were tested for the ability to express lacZ by direct staining of duplicate wells. The titer of the virus produced by the positive cells was assayed by single addition of 50 μl of medium to HT-1080 human tumor cells grown to 20% confluency in 6-well microliter plates with 3 ml medium per well and in the presence of 4 μg/ml of polybrene. The titer was assayed by determining the number of HT-1080 cells that stained positively for expression of the lacZ gene. Typically, the titer was $1\times10^5$ to $1\times10^6$.

Retrovirus Infection of Mouse MSCs

Primary cultures of mouse MSCs were prepared as described above. After 3 days, the non-adherent marrow cells were discarded and fresh medium was added. The cells were then infected with the retrovirus in the presence of 4 μg/ml of polybrene by addition of ¼ volume of fresh supernate medium from stably transfected producer cells that had the highest titer of virus production. The infection was repeated on two additional successive days. The cells were then either stained directly for lacZ expression or were divided into larger dishes and placed under selection with 0.4 mg/ml of G418 (active concentration). About 15 to 20% of primary cultures were positive for lacZ and most of the cells that survived G418 selection were positive for lacZ.

Lipofectamine Transfection

Primary cultures of MSCs were grown for 10 days in α-MEM containing 10% FBS. After trypsinization and light scraping, the cells were seeded in a 6-well plate at a density of $10^5$ cells per well. The cells were grown for 2 days, then washed 2 times with PBS and incubated with a DNA-lipofectamine complex. The DNA-lipofectamine complex was prepared as follows: 6 μl of lipofectamine (GIBCO/BRL) were mixed with 1 μg of LNCZ DNA in 200 μl of α-MEM, incubated at room temperature for 30 min, and added to one well of a 6-well plate containing MSCs in 800 microliter α-MEM. After 6 hour incubation at 37° C., the DNA-lipofectamine complex was replaced with 2 ml of α-MEM containing 10% FBS. The cells were stained for lacZ or placed under G418 selection after 18 hour incubation in FBS-containing medium. Positive clones were obtained, but they grew slowly, apparently because the cell density was too low after the G418 selection. To circumvent this situation, three different strategies can be used: cells are plated at higher densities; co-culture cell culture inserts are placed over surviving clones early in the selection process and fresh MSCs or pieces of bone in the inserts are placed (see Table 1) on a daily basis to provide the necessary cell factors to stimulate growth; at the time that selection with G418 has killed many of the non-transfected cells, the cultures are reseeded with MSCs that have been infected with a variant of the retrovirus LNCX (FIG. 1) in which the lacZ gene is replaced with a selectable gene for thymidine kinase. Therefore, the MSCs stably transfected with retrovirus are used to provide the necessary cytokines, growth factors, and cell interactions required for the initial growth of the transfected MSCs during selection in G418. The cells infected with the retrovirus may be then removed by negative selection with gangcyclovir.

Delivery Methods

Nuclear Injections

Nuclear injections are highly efficient as a means of transfecting some cells. Cells were plated in 60-mm dishes containing a 22×22 mm coverslip marked with a circle to delineate the area for microinjection. Cells were incubated in medium containing 0.1% CS for 5 days to induce growth arrest before microinjection. Under these conditions between 8 and 15% of the cells incorporated [$^3$H] thymidine during continuous labeling for 24 hours between days 5 and 6. Microinjection was performed using a Zeiss Axiovert inverted-microscope equipped with an Eppendorf microinjector and micromanipulator using commercially purchased glass-capillary femtotips (Eppendorf). All cells within a delineated area of the coverslip (usually 150–200) were microinjected into the nucleus with DNA at concentrations ranging from 0.01–10 μg/μl in 10 mM Tris buffer (pH 7.6). The injected cells are then expanded and assayed as described above.

Electroporation

MSCs are treated with 0.25% trypsin and 1 to 5 mM EDTA for 5 minutes at room temperature and then harvested by scraping. The cells are pelletted by centrifugation at 4,000×g for 10 minutes, and then are washed twice by resuspending the pellet in ice cold PBS (pH 7.4). MSCs are resuspended at $2\times10^6$ cells per 0.8 ml and aliquoted into an electroporation cuvette (0.4 cm gap). The cells are incubated for 10 minutes on ice, DNA is added to the suspension (5–50 μg), and the cells are chilled for an additional 10 minutes. The cell suspension is then electroporated using a commercial instrument (BioRad Gene Pulser; model 1652076) at an empirically determined field strength which yields the greatest percentage of cells that retain the exogenously added DNA. To determine the appropriate field strength for MSCs, titrations have been performed ranging from 0.25–2.5 kv/cm. Electroporation efficiency was monitored by introducing a lacZ gene (LNCZ vector) and then staining cells 48 to 72 hours after electroporation.

Assays hGH

Expression of the hGH gene is monitored by assaying medium from clones of cells grown in 6-well microliter plates with an enzyme linked immunoabsorbent assay with a commercially available kit (GIBCO/BRL). In this assay, 0.1 ml of 2×diluent buffer is added per well of a microtiter plate. After 5 minutes, 0.1 ml of test sample is added and the plate is incubated at 37° C. for 30 minutes. The wells are washed 5 times and 0.2 ml of primary antibody is added per well. The samples are incubated at 37° C. for 30 minutes, and washed 5 times. Then 0.2 ml of substrate buffer containing 0-phenylenediamine substrate is added. Samples are incubated at room temperature for 30 minutes and the reaction is stopped by addition of 0.1 ml of 2 N sulfuric acid. The absorbance of the sample is assayed at 490 nm.

Ob Protein

Cells are assayed for expression of the OB gene using a protein radioimmunoassay of cell medium. The primary antibody for human OB protein was raised in rabbits against recombinant protein synthesized in an *E. coli* expression system and purified to homogeneity. The human protein is highly homologous to the mouse and, therefore, anti-human antibodies should cross-react with the mouse protein. If they do not, the short mouse cDNA (619 nt) is expressed in *E. coli*, the protein is purified and antibodies are prepared. Alternatively, synthetic peptides having the mouse sequence are purchased and these are used to prepare antibodies. For the assay, recombinant human Ob protein was radiolabeled with $^{125}$Iodine by the BoltonHunter method followed by gel filtration purification using Sephadex G-25. The specific activity obtained was 30 μCi/μg. Samples for assay (0.2 ml) were preincubated with primary antiserum (1:2000 dilution) in phosphate buffered saline containing 0.1% Triton X-100 for 16 hours at 4° C. in a total volume of 0.4 ml. $^{125}$I -Ob protein (30,000 cpm carried in 100 μl) was then added and the incubation was continued for an additional 24 h. The bound Ob protein (12±1%; nonspecific binding 1.4±0.1%) was immunoprecipitated by the addition of 0.1 ml sheep anti-rabbit IgG serum (Antibodies, Inc., Davis, Calif.), 0.1 ml normal rabbit serum (GIBCO/BRL, Gaithersburg, Md.), and 0.1 ml of 10% polyethylene glycol. The tubes were centrifuged for 15 minutes (2200 rpm), unbound label was decanted and the radioactivity in the pellet was counted in a Packard 5000 gamma counter (Downers Grove, Ill.). The concentration of Ob protein in unknown samples was calculated using Rodbard's unweighted four parametric logistic model. The limit of detection of this assay is 0.39 ng/ml. The intraassay variance is 11.6% at 12 ng/ml with an interassay variance of 20.8% at 13.1 ng/ml.

Human Factor IX

Expression of the gene encoding factor IX is assayed using a commercially available ELISA (American Bioproducts Company) under conditions similar to those used in the hGH assay (above). The standard curve ranged from 1–50 ng/ml$^{-1}$ and the limit of sensitivity was 1 ng/ml$^{-1}$. The assay did not cross-react with mouse factor IX.

Example 4

Sustained Expression of the Three Genes at Physiologically Important Levels by Systemic Infusion of Stably Transfected MSCs into Mice Experiments with the OI transgenic mice (Tables 2 and 3) have demonstrated that cultured MSCs can serve as stem-cell-like precursors of bone, cartilage and other mesenchymal tissues after systemic infusion. Therefore, MSCs expressing hGH, the Ob protein or factor IX are infused into irradiated and nonirradiated mice to evaluate sustained expression of the genes in vivo.

Infusion of MSCs

Initially, MSCs are infused into mice under conditions such as those described in Table 2 (3-week old mice: 300 or 700 Gray irradiation; intraperitoneal injection; $1\times10^6$ MSCs; and $2\times10^8$ whole marrow cells). In addition, intravenous infusion is compared to intraperitoneal; and lower levels of X-ray irradiation are employed. Also, the cells are infused into embryos by Cesarean section. In preliminary trials, 50 μl of $5\times10^4$ ES were injected into the amnion of seven 13-day embryos; 6 of 7 were delivered as viable pups. Therefore, intrauterine injection of MSCs is feasible.

Growth Curves

Effective in vivo expression of hGH should increase the growth rate of mice and expression of the Ob protein should induce starvation. Therefore, the weight and size of the treated mice and of control littermates are monitored.

Assays for Gene Expression

Blood is obtained from the retro-orbital plexus of mice at 1 week, 1 month, 3 months, 5 months, 10 months, and 20 months after infusion of the MSCs. hGH and factor IX are assayed by ELISA, and the Ob protein is assayed with a radioimmune assays. In addition, if measurable increases in human factor IX are obtained with ELISA, the procedure described in Smith et al. (1993) Mature Genet. 5:397–402, to assay biologically active human Factor IX. In this procedure, human Factor IX was first captured in a microtiter well with the monoclonal antibody, BGIX1, and then activated by Factor Xla. The active Factor IX, in combination with Factor VIII, converted Factor X to Xa. Factor Xa cleaved the chromogenic substrate, S2765, yielding a yellow product. BGIX1-coated microliter plates and Factor VIII were purchased from Elcatech, Inc. (Winston-Salem, N.C.). Factor Xia was purchased from Enzyme Research Labs, Inc. (South Bend, Ind.).

Factor X, phospholipid solution, S-2765, and the thrombin inhibitor, 1-2581, were purchased from Kabi Pharmacia Hepar, Inc. (Franklin, Ohio). Four buffers were prepared: A, 50 mM Tris, 150 mM NaCl, 1% BSA, pH 7.5; B, 150 mM Tris, 5 mM $CaCl_2$, 10 mg/ml gelatin, pH 7.6; C, 50 mM Tris, 10 mM CaCl$_2$, pH 7.5; D, 50 mM Tris, 150 mM NaCl, pH 8.4. The Factor VIII/X reaction mix was prepared fresh by mixing equal quantities of the following stocks: Factor VIII, 5 U/ml in buffer A; Factor X, 1 U/ml in buffers; 1–2581, 34 µg/ml in buffer A; CaCl$_2$, 25 mM in water; and phospholipid. Plasma samples were diluted in buffer A and 100 µl was added to each microtiter well. The plate was incubated for 90 minutes at room temperature and then washed five times with buffer B. 100 µl of Factor XIa (2 µg/ml in buffer C) was added to each well. After 30 minutes at 37° C., 100 µl of S2765 (0.5 mM in buffer D) was added to each well and the plate was incubated for 10 minutes at room temperature before the reaction was stopped by adding acetic acid to a final concentration of 10%. Absorbances at 405 nm were determined using a Bio-Rad microplate reader. The standard curve, prepared with dilutions of human normal pooled plasma, was linear from 3–25 ng/ml. The assay did not cross react with mouse Factor IX. Factor IX, levels of 250 ng/ml or 5% of normal are generally considered therapeutic and 100 to 150 ng/ml are considered beneficial.

Example 5
Sustained Expression of the Genes at Physiologically Important Levels by Placing the MSCs in Subcutaneous Diffusion Chambers Cells implanted in subcutaneous diffusion chambers have at least two distinct advantages for use in therapy of human patients: Immune responses are circumvented; and when implanted in capsules in mice (Benayahu, 1989, J. Cell Physiol.140:1–7), rats (Mardon et al., 1987, Cell Tissue Res. 250:157–165) or rabbits (Friedenstein et al., 1987, Cell Tissue Kinet. 20:263–272), they survive for at least 6 weeks (Wakitani, 1994, J. Bone and J. T. Surgery 76A:579–592), apparently because they persist as bone, fibrous tissue or cartilage that does not require vascularization (Benayahu et al., 1989, Supra; Mardon, et al., 1987, Supra; Owen et al., 1988, In: Cell and Molecular Biology of Invertebrate Hard Tissues, Wiley Chicester, CIBA Foundation Symposium, 136:42–60; Friedenstein et al.,1987, Supra).

Preparation of Chambers

Diffusion chambers are assembled from commercially available components (Millipore Corp.) and used as described in previous reports (Benayahu et al., 1989, Supra; Mardon et al., 1987, Supra). Briefly, membrane filters with pore size are glued to one side of each of two plastic rings with acryloid glue. The two rings are then glued together to form a chamber, the dimensions are 9 mm inner diameter and 2 mm thick with a volume of about 127 mm$^3$. From 10$^4$ to 10$^7$ MSCs are inoculated into the chambers through a hole in one ring and the hole is sealed with a tapered plastic plug coated with glue. The chambers are implanted into mice either subcutaneously on the back or intraperitoneally under anesthesia. Initially, one or more chambers are inserted into freshly weaned mice (3 weeks). Subsequently, chambers are inserted in 1 week old mice. For the experiments with the 1 week old mice, smaller chambers are prepared from discs (5 mm, inner diameter) cut from plastic tips for micropipettes.

Assays

Blood is obtained from the retro-orbital plexus at 1 week, 1 month, 3 months, 5 months, 10 months and 20 months after implantation of the chambers. The plasma is assayed for hGH, Ob protein and factor IX as described above.

Example 6

Figure 2:
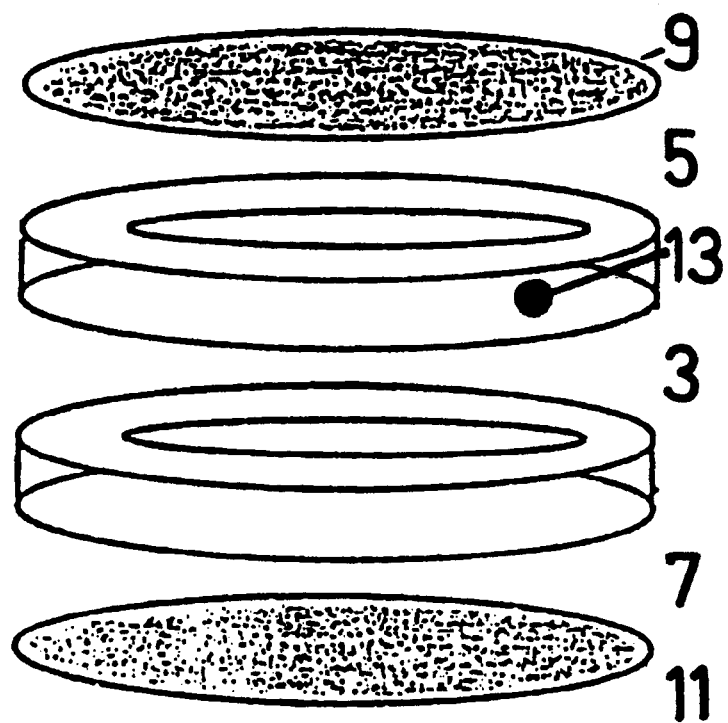
FIG. 2 is a schematic illustration of a diffusion chamber.

Referring to FIG. 2, the diffusion chamber (1) may have a chamber barrel (3) having two ends, a first end (5) and a second end (7). The barrel may be comprised of one or more rings secured together by non-toxic means. The chamber is fitted at each end with a filter, a first filter (9) and a second filter (11). The filters are porous to factors, for example, proteins, such that the factors may pass between the chamber and the mammal. The filter pores size may be about 0.25 µm or smaller, preferably about 0.1 µm. The filters may be made of plastic, teflon, polyester, or any inert material which is strong, flexible and able to withstand chemical treatments. The filters may be secured in position with rubber gaskets which may also provide a tighter seal. Optionally, the barrel portion of the chamber may have an opening (13) which may be covered by a cap (not shown). The cap may be a screw on type of self sealing rubber and fitted to the opening. Inserting cells into the chamber contents may thus be performed by accessing the opening by removing the cap and inserting cells using an ordinary needle and syringe. The chamber may be made of any substance, such as but not limited to, plastic, teflon, lucite, titanium, or any inert material, which is non-toxic to, and well tolerated by, mammals. In addition, the chambers should be able to survive sterilization.

The chamber may be implanted in the following nonlimiting ways: subcutaneously or intraperitoneally, for example. The chamber may be removed about 24 to about 30 hours after implantation. Alternatively, a refillable chamber may be employed such that the chamber may be re-used for treatments and emptied following treatments.

Example 7
Administration of Isolated MSCs Directly into Rat Brains
Preparation of Donor MSCs and Astrocytes Human MSCs (Owen et al., 1988, in Cell and Molecular Biology of Vertebrate Hard Tissues, Ciba Foundation Symposium 136, Chichester, UK, pp. 42–60; Caplan, 1991, J. Orthop. Res. 9:641–650; Prockop, 1997, Science 276:71–74; Pereira et al., 1995, Proc. Natl. Acad. Sci. 92:4857–4861; Pereira et al., 1998, Proc. Natl. Acad. Sci. 95:1142–1147) were grown from aspirates taken from the iliac crest of normal male and female volunteers, aged 19 to 46 years old. Aspirates were diluted 1:1 with α-MEM/10% FBS and were centrifuged through a density gradient (Ficoll-Paque Plus; 1.077 g/ml, Pharmacia, LKB Biotechnology Inc., Piscataway, N.J.) for 30 minutes at 1000×g. After the supernatant and the interface were combined, the mixture was diluted to about 40 ml with α-MEM/10% FBS, and was again centrifuged. The nucleated cells, i.e., the MSCs, were suspended at a concentration of 1×10$^7$/ml in α-MEM/10% FBS and the cells were plated at 3×10$^6$/cm$^2$ in 25 cm$^2$ culture dishes. The MSCs were incubated for 3 days and the non-adherent cells were removed by replacing the medium in the culture. After the MSC cultures reached confluency, the MSCs were lifted from the plates by incubation with 0.25% trypsin and 1 mM EDTA at 37° C. for 3 to 4 minutes. The MSCs were diluted 1:2 or 1:3 and the procedure for preparing the MSCs was repeated for 3 to 5 passages. Beginning with the second passage, 5 ng/ml of platelet derived growth factor (PDGF-AA; GIBCO/BRL, Grand Island, N.Y.) was added to the medium.

For the isolation of rat MSCs, tibias and femurs obtained from 8–12 week old Lewis/SsNHsd female rats were dissected (Harlan Sprauge Dawley, Ind.). The ends of the bones were cut, and the marrow was extruded using 5 ml of DMEM (GIBCO/BRL, Grand Island, N.Y.) using a needle and syringe. Between 100–200×10$^6$ whole marrow cells were plated on a 175 cm$^2$ tissue culture flask in DMEM/10% FBS. After 24 hours, the non-adherent cells were removed by replacing the medium. The medium was replaced every 2 to 3 days as the cells were grown to confluency. The cells were lifted as before by incubation in the presence of 0.25% trypsin and 1 mM EDTA, following which the cells were passed three or four times and were then stored frozen until use.

Primary cultures of astrocytes (Azizi, 1996, Ann. Neurol. (suppl)121:T236) were obtained from the brains of albino Sprague-Dawley adult rats (Harlan Sprague Dawley). After the heads of the mice were decapitated, the brains were removed under aseptic conditions and were floated in cold PBS over ice. The meninges and the brain stem were removed and discarded. The forebrain was mechanically dissociated into small pieces of tissue and the tissues were incubated at 37° C. for 30 minutes in 2.4 units/ml of dispase (GIBCO/BRL, Grand Island, N.Y.). At 10 minute intervals, the tissues were dissociated by flushing them through a large bore pipette. The dissociated tissues were centrifuged and the supernatant was discarded. The residue from each brain was suspended in α-MEM and was plated in two 175 cm$^2$ culture flasks, each in a medium of α-MEM/10% FBS. The non-adherent cells and the debris were removed by changing the medium after 48 hours, and then changing the medium every 4 days for about 2 weeks until the cultures were confluent. To remove loosely adherent cells, the confluent cultures were treated with 2.4 units/ml dispase for 15 minutes at 37° C., and the cultures were shaken on a rotary shaker at 120 rpm for 2 hours. The detached cells were discarded. Fresh medium was added to the adherent cells and the cultures were reincubated for 24 to 48 hours. Treatment with dispase to remove loosely adherent cells was repeated three times over a period of about 1 week.

For antibody staining, the cells were lifted from the plates by incubation with 0.25% trypsin for 1 to 3 minutes. The cells were then subcultured in chambered slides. To label the nuclei fluorescently, the MSCs and the astrocytes were incubated in the presence of 1 μg/ml bis-benzamide (Sigma Chemical Company, St. Louis, Mo.) for 24 hours prior to implantation. At one to two hours prior to implantation, the cultures were washed three times with sterile buffered saline and were lifted from the plates by incubation with 0.25% trypsin for 1 to 3 minutes. The trypsin was neutralized by adding medium containing 20% serum, and the cells were isolated by centrifugation. The cells were suspended as a slurry of about 10,000 cells/liter in α-MEM without serum.

Neurotransplantation of Cells

Adult Sprague-Dawley albino rats (weighing 200 to 300 grams each) were anesthetized in a sealed chamber using 3% halothane in oxygen. Anesthesia was maintained by intramuscular injection of a mixture of 6 mg/kg xylozine and 60 mg/kg ketamine. The animals were transferred to a sterotaxic apparatus in a clean field. A 2 to 5 mm incision was made in the scalp, 2 mm lateral to the bregma. A burr hole was made in the bone at a position 3 mm lateral to the bregma using a dental drill. About 10 μl of the cell suspension was slowly injected over 30 minutes into the striatum at a depth of 4 to 5 mm deep from the surface of the brain. The wound was closed with interrupted surgical sutures, and the animals were treated with 0.6 mg/kg of xylozine and 6 mg/kg of ketamine. At 5, 14, 30 and 72 day intervals, the rats were sacrificed by intracardiac perfusion under deep anesthesia using xylozine and ketamine. Perfusion was performed using ice-cold phosphate buffered saline, followed by 3% buffered paraformaldehyde, and then followed by 10% sucrose. The brains were removed, the forebrains were trimmed, and samples comprising sections of the brain were frozen immediately.

Immunohistology of Implanted Cells

Ten micron tissue sections were prepared using a cryostat. The transplant site in the brain was located by microscopically identifying the fluorescently labeled cells in the tissue sections. Frozen sections were attached to the gelatin coated slides and were quickly immersed in cold acetone for 5 minutes and stored at −20° C. for further processing. The cells in the chambered slides were fixed with acetone for 5 minutes. Immunocytochemistry was performed at room temperature. The cells and the tissue sections were treated with blocking antibodies comprising 2% goat serum and 5% fetal bovine serum for 30 minutes. In experiments requiring the labeling of collagen and vimentin, the cells were further treated with Triton X-100 for 30 minutes and were then were rinsed in PBS. Primary antibodies were applied (Table 4) for 1 to 2 hours to cells in the chambered slides. These antibodies were applied for 24 hours in the case of tissue sections. The secondary antibodies used were species-specific IgGs coupled to either FITC or rhodamine.

Fluorescently labeled cells were visualized and photographed using a fluorescent microscope. The number of fluorescently labeled nuclei were counted in eight to ten tissue sections, cut from rostral to caudal limits of the striaturn. This procedure was repeated on each brain by two individuals, who used alternate sections. Only the clearly labeled nuclei were counted. Dead and lysed cells left a bluish hue in the surrounding tissue and no clear nuclear staining. The observed numbers were extrapolated to the total number of sections in order to estimate the number of surviving engrafted cells.

Donor MSCs and Astrocytes Precursors

Figure 3:
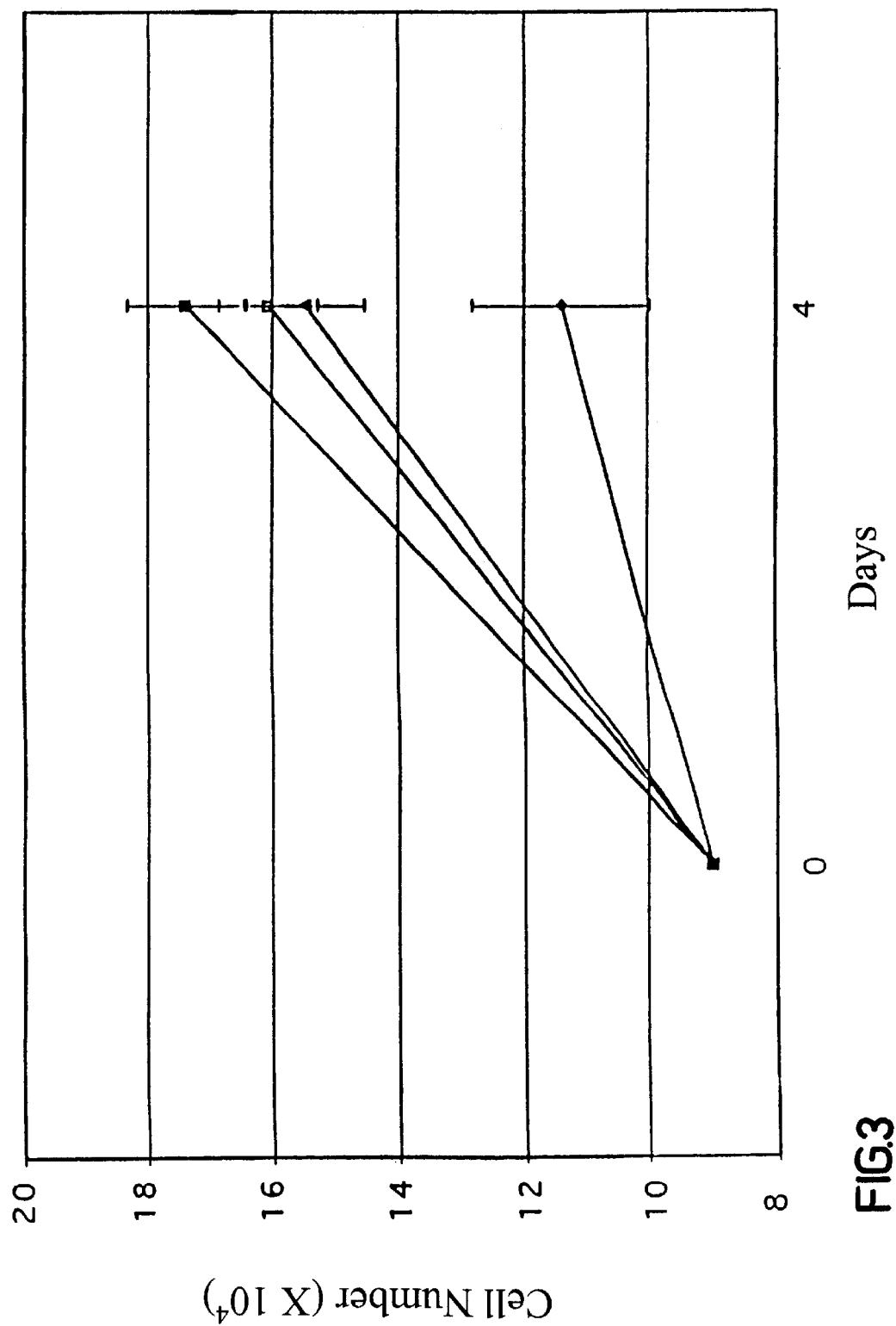
FIG. 3 is a graph depicting the effect of PDGF-AA on the growth of human of MSCs. The following symbols are represented: ◆, control; ▲, __ng/ml PDGF; ☐, __ng/ml PDGF; ■, __ng/ml PDGF.

MSCs obtained from human bone marrow were isolated by their adherence to plastic and were grown for 3 to 5 passages. As indicated in FIG. 3, the addition of PDGF-AA increased the growth rate of the cells. Therefore, PDGF-AA was added to cells at passages 2 to 5 in order to obtain adequate numbers of human MSCs. However, rat MSCs grew adequately without the addition of PDGF-AA. Astrocytes were also isolated because of their tight adherence to plastic cultures dishes. Astrocytes were harvested after primary culture for about 3 weeks.

As indicated in Table 4, human MSCs stained heavily for fibronectin, collagen I and human HLA-ABC. Human MSCs stained faintly for vimentin and were negative for glial fibrillary acidic protein, whereas rat astrocytes were positive for both. Rat astrocytes stained poorly for fibronectin and were negative for collagen I and human HLA-ABC. Rat astrocytes were also negative for von Willebrand factor and galactocerebrosidase C.

Figure 4:
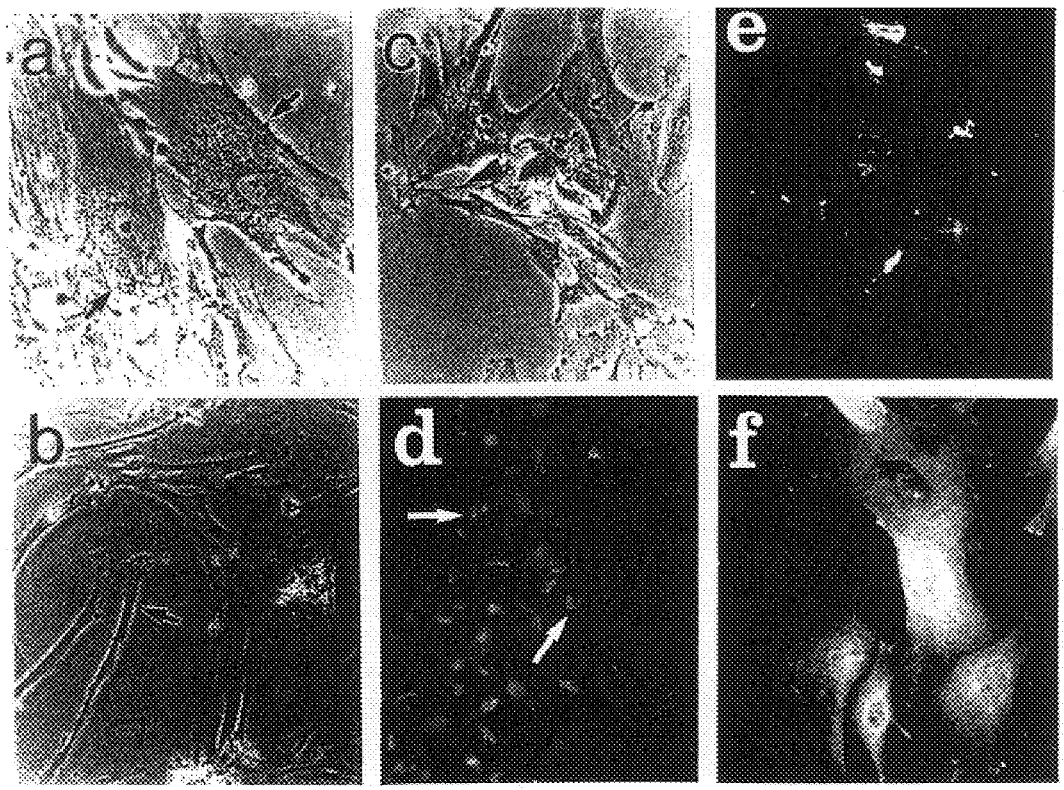
FIG. 4 comprising Panels A–F, is an image of photomicrographs illustrating the morphological characteristics of MSCs and astrocytes in culture. Panel A and Panel B depict two types of human MSCs: flat and elongated. Panel C depicts rat MSCs. Panel D depicts fluorescent labeled nuclei of human MSCs prior to implantation. Panels E and F depict indirect immunofluorescent staining of astrocytes with antibodies against vimentin and glial fibrillary acidic protein.

It has been previously described that human MSCs become relatively homogeneous in appearance as these cells are passaged in culture (Bruder et al., 1997, J. Cell Biochem. 64:278–294). However, in the present study, two distinct populations were seen. These included a population of large flattened cells and a population of relatively elongated or spindle shaped cells (FIG. 4, Panels A and B). In rat MSCs, two distinct populations of cells having similar morphologies were also seen (FIG. 4, Panel C). The rat brain astrocytes were more dendritic in appearance (FIG. 4, Panels E and F).

Survival of Cells after Injection in the Striatum

Figure 5:
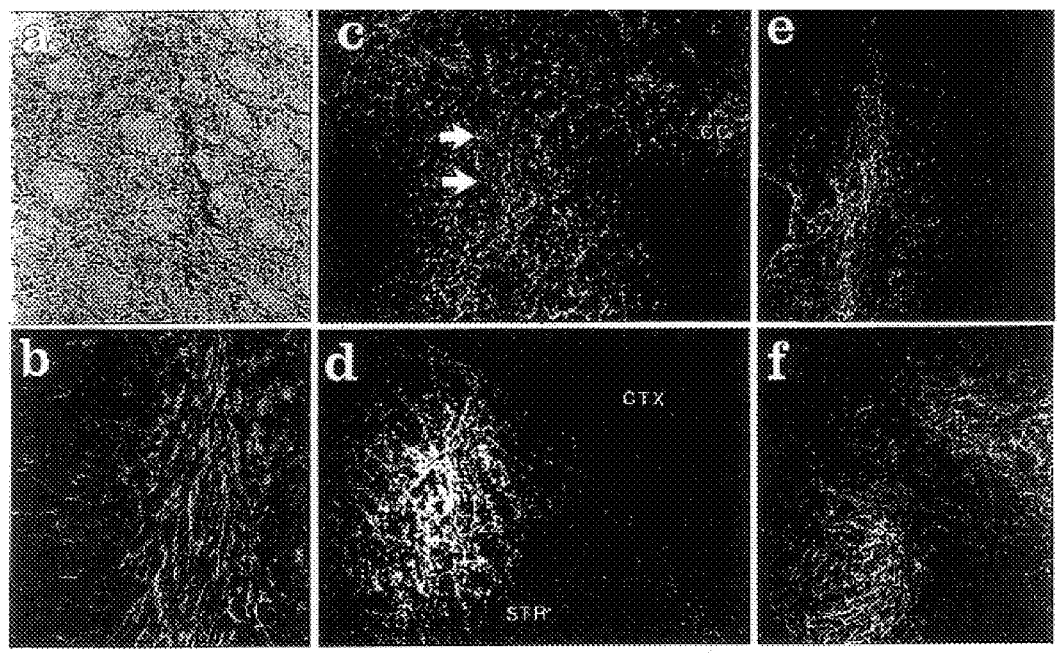
FIG. 5 comprising Panels a–f, is an image of photomicrographs depicting the site of implantation of bone marrow stromal cells in the striatum of adult rats. Panel a depicts the site of implantation of human MSCs after 14 days. Panel b depicts an adjacent section to that shown in a, wherein human MSCs were stained with antibodies to HLA-ABC. Panel c depicts an adjacent section to that in a, wherein cells were examined for nuclear fluorescence of human MSCs. Panel d depicts the site of implantation of human MSCs after 72 days. Panel e depicts the same site of implantation as in Panel d of human MSCs after 30 days. Panel f depicts the site of implantation of human MSCs after 14 days. These cells were examined by nuclear fluorescence.

The MSCs and the astrocytes were injected in the corpus striatum of rat brains using minimal perfusion pressure. Five to 72 days later, the rats were killed and sections of their brains were obtained. Examination of sections stained with hematoxylin and eosin indicated that there was no significant gliosis around the implantation site of either the rat astrocytes or the MSCs (FIG. 5, Panel a). Fluorescently labeled cells were readily detected in the brain sections. Rat astrocytes, as previously shown in the prior art, readily engrafted (Andersson et al., 1993, Int. J. Dev. Neurosci.11:555–568; Azizi, 1996, Ann. Neurol. (suppl)121:T236; Zhou et al., 1992, J. Comp. Neurol. 317:145–155). Similar results were obtained using rat MSCs (FIG. 5, Panel f) and human MSCs (FIG. 5, Panels b–e). As indicated in Table 5, from about 20,000 to 42,000 cells were present in the recovered brains. Since the number of the cells injected varied from 100,000 to 120,000, about 20% of the infused human MSCs were recovered after 5 to 72 days. Moreover, there appeared to be a decrease in the number of the infused human MSCs recovered between days 30 and 72. In the case of rat MSCs, 33,000 cells or about 30% were recovered 14 days after infusion (FIG. 5f).

Migration of the Implanted Cells

Figure 6:
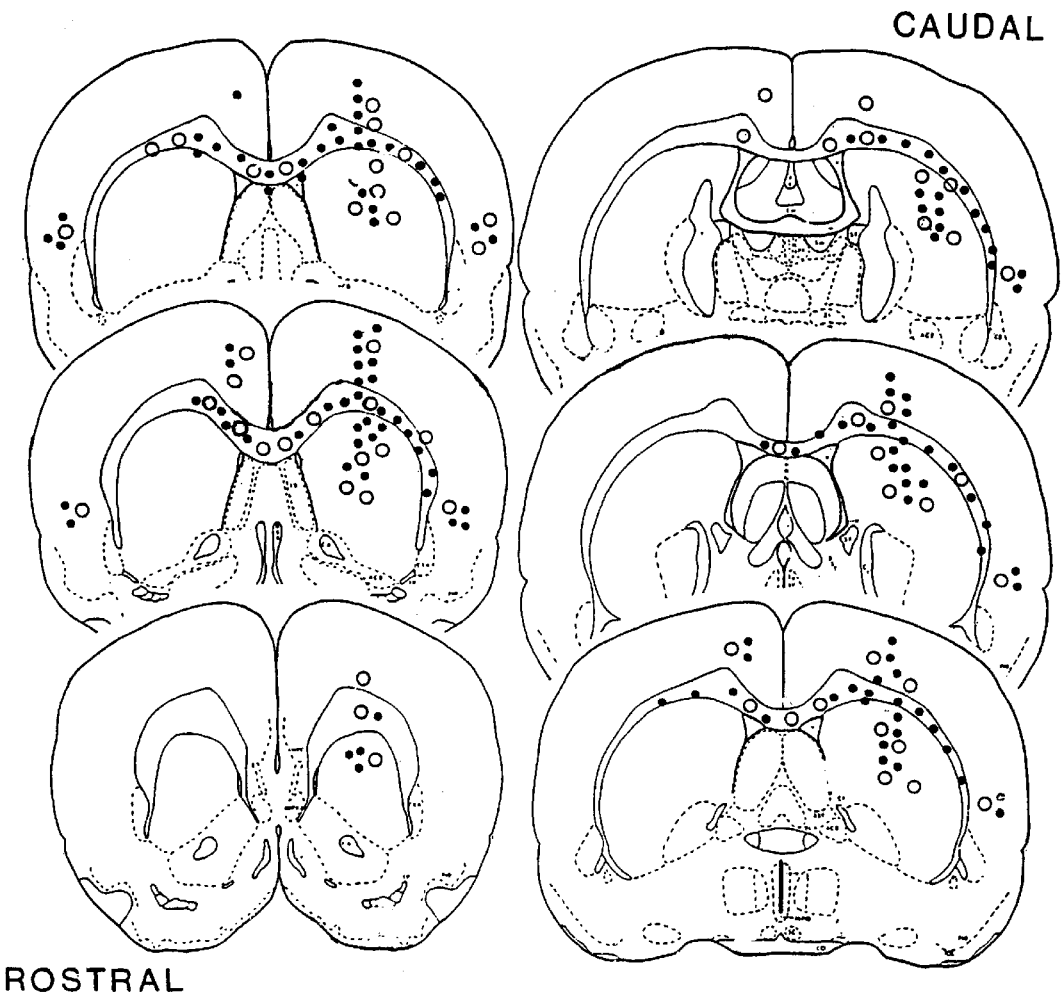
FIG. 6 is a series of line drawings of rat forebrain, illustrating the migration of MSCs through the brain. The drawing is a composite from brains examined at 4, 14, 30 and 72 days after cell infusion. The pattern of implantation and migration of human MSCs is similar to that of rat astrocytes. The outlying cells, located in the temporal cortex and areas of corpus callosum farthest from the injection sites, were first to disappear. The following symbols are represented: ●, human MSCs; ○, rat astrocytes.

It has been previously described that implanted rat astrocytes migrate through layers of the brain (Andersson et al., 1993, Int. J. Dev. Neurosci. 11:555–568; Zhou et al., 1992, J. Comp. Neurol. 317:145–155) in a manner similar to the migration seen with implanted neural stem cell or with a transformed line of the neural stem cells (McKay, 1997, Science 276:66–71). In the present invention it has been discovered that MSCs migrated in a similar fashion. Donor cells were found in multiple areas of the brain, including the contralateral cortex (FIG. 6). The cells persisted in the sites to which they migrated. The heaviest concentration of cells was found around the rostrocaudal axis in the striatum and along the corpus callosum. There were fewer cells in the cerebral cortex. Clusters of labeled cells were consistently observed in the temporal lobe regions at all time points examined. At day 72, fewer cells were found in the outlying cortical regions, an observation consistent with the apparent decrease in cell number between day 30 and 72 (Table 5).

Immunohistology of Implanted Cells

Figure 7:
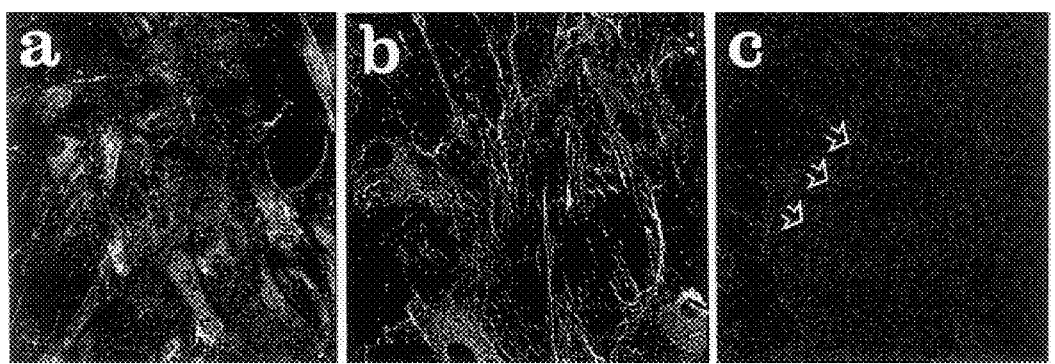
FIG. 7 comprising Panels a–c, is an image of photomicrographs depicting antibody staining to collagen I and fibronectin. Panel a depicts human MSCs stained with antibodies to collagen I prior to implantation. Panel b depicts human MSCs stained with antibodies to fibronectin. Panel c depicts a section of a rat brain stained for fibronectin 5 days after implantation of human MSCs.

Immunostaining of sections demonstrated that engrafted human MSCs were also detected throughout the brain (FIG. 6) when antibodies to HLA-ABC were used (FIG. 5, Panel b). Although human MSCs stained with antibodies to collagen I prior to implantation (FIG. 7, Panel a), no staining with the same antibodies was seen after implantation. Thus, the MSCs ceased synthesis of type I collagen after integration into brain tissue. Staining of the cells with antibodies specific for fibronectin was observed prior to implantation (FIG. 7, Panel b) and was also observed 5 days after implantation (FIG. 7, Panel c).

The results of neurotransplantation experiments establish that human MSCs infused into rat brain can engraft, migrate, and survive in a manner similar to engraftment, migration and survival of rat astrocytes. Rat MSCs behaved in a similar manner to rat astrocytes. Thus, the rat and human cells behave in a similar manner. The data presented herein has established that at least a subset of cells that are isolated from the bone marrow by their adherence characteristics to plastic culture dishes, may also participate in the same pathway as astrocytes. The results establish that MSCs are therefore useful vehicles for both cell and gene therapy for treatment of a variety of diseases in humans. In addition, since the transplanted MSCs ceased synthesis of collagen type I, these cells are much more suitable for neurotransplantation than are fibroblasts which are known to continue to produce large amounts of collagen following transplantation and which therefore induce fibrosis at the site of transplantation.

MSCs have several advantages as cells for neurotransplantation. In particular, they can be readily obtained from bone marrow and expanded in culture. Also, a patient's own MSCs can be employed for the therapy, thus circumventing any attending problems of host immunity and graft versus host disease. In addition, the cells may be genetically engineered for treatment of diseases in human.

Example 8

Coculture of MSCs with Astrocytes: Differentiation of MSCs into Astrocytes

Human MSCcs at a concentration of $2 \times 10^5$ cells were cocultured with rat astrocytes at a concentration of $1 \times 10^5$ cells in 10 ml of medium that consisted of MEM plus 30% FBS Sigma). The human cells were fluorescently labeled with α-human HLA-ABC prior to coculture. Following 5 days of coculture, about 2% of the human cells also stained positive for glial fibrillary acidic protein. Since glial fibrillary acidic protein is a marker for early astrocytes, these results demonstrate that a fraction of the human MSCs had differentiated into astrocytes during coculture with rat astrocytes.

TABLE 1

Conditions for Growth of Primary and Secondary Cultures of MSCs

| MSCs | Culture Conditions | Cells per Well × $10^5$ | APase[a] (mmol min/mg) | TRAP[a] (mmol min/mg) |
|---|---|---|---|---|
| Primary | Standard[a] | 2.0 | 42.6 | 144 |
|  | Co-cultured[b] | 6.41 | 22.3 | 102 |
|  | Co-cultured[c] (Matrigel) | 6.94 | 42.0 | 105 |
| Secondary[d] | Standard | 1.33 | 2,052 | 72 |
|  | Co-cultured | 7.40 | 362 | 60.6 |
|  | Co-cultured (Matrigel) | 5.08 | 506 | 59.2 |

[a]Whole marrow cells (20 × $10^6$) from 6-week old mice were cultured in individual 9.5 cm² wells in a 2 ml of 10% FCS and α-MEM. Non-adherent cells were removed on day 3 and the incubation was continued in fresh medium until day 7. APase and TRAP were assayed.
[b]Co-cultured with pieces of bone (one-half femur and one-half tibia) in cell culture inserts (23 mm; 3 μm pore size; Becton Dickinson).
[c]Same as [b], with inserts coated with Matrigel.
[d]Primary cultures on day 10 were detached with 0.25% trypsin and 1 mM EDTA for 5 minutes at 37° C. followed by gentle scraping. Cells from one well (2 × $10^5$) were diluted 1:4 and cultured in 9.5 cm² wells for 7 days with changes of medium on day 3 and day 6.
[e]APase and TRAP activities were per mg total protein.

TABLE 2

Experiments with (a) Transgenic Mice as Recipients; (b) Normal MSCs as Donor Cells; and (c) Decreasing X-Ray Done

| Recipient mice | X-ray (cG) | Donor Cells | | Bone replacement at 1 month (%)[c] |
|---|---|---|---|---|
| | | MSCs | Whole marrow | |
| Transgenic (3 weeks) | 700 | 0.7 × $10^6$ (N)[a] | 15 × $10^6$ (TG)[ab] | 10 to 45% (n = 3) |
| Transgenic (3 weeks) | 350 | 1.2 × $10^6$ (N) | 2 × $10^6$ (TG) | 28 to 60% (n = 4) |
| Transgenic (3 weeks) | 175 | 1.2 × $10^6$ (N) | 2 × $10^6$ (TG) | 0 to 40% (n = 4) |

[a](N), normal; (TG), transgenic.
[b]MSCs removed from whole marrow cells before infusion by incubation on plastic culture dish for 4 hours at 37° C.
[c]Values obtained using a semi-quantitative assay.

TABLE 3

Experiments with (a) Transgenic Mice as Recipients; (b) 10-Fold Increase in Whole Marrow Cells as Donor Cells; and (c) Decreasing X-Ray Dose

| Recipient mice | X-ray (cG) | Donor Cells[a] MSCs | Donor Cells[a] Whole marrow | Bone replacement at 1 month (%)[b] |
|---|---|---|---|---|
| Transgenic (3 weeks) | 700 | | $5 \times 10^6$ (N)[a] | 20 to 38% (n = 3) |
| Transgenic (3 weeks) | 350 | | $16 \times 10^6$ (N) (n = 3) | 50 to 78% (n = 4) |
| Transgenic (3 weeks) | 350 | | $5 \times 10^6$ (N) | 22 to 45% (n = 4) |

[a](N) whole marrow from normal mice without any treatment to remove MSCs.
[b]Values obtained using a semi-quantitative PCR assay.

TABLE 4

Immunostaining of Human MSCs and Rat Astrocytes

| Antibodies | Dilution | Human MSCs | Rat astrocytes |
|---|---|---|---|
| Fibronectin (Sigma) | 1:400 | +++ | − |
| Collagen I (Biodesign) | 1:10 | ++ | − |
| HLA-ABC (Pharmingen) | 1:100 | ++ | − |
| Vimentin (Sigma) | 1:40 | +/− | +++ |
| Glial Fibrillary Acidic Protein (Sigma) | 1:20 | − | ++ |
| Galactocerebrosidase C (Sigma) | 1:50 | NA[a] | − |
| von Willebrand Factor (Sigma) | 1:200 | NA | − |

[a]NA, not assayed

TABLE 5

Recovery of Fluorescently Labeled Human MSCs from Rat Brain

| Days after infusion | Labeled cells per brain |
|---|---|
| 5 | 27,300[a] |
| 14 | 30,200 |
| 30 | 41,800 |
| 72 | 19,900 |

[a]Total counts on alternative sections by two different observers differed by less than 20%.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of directing the differentiation neural of an isolated stromal cell into a neural cell, comprising culturing said isolated stromal cell in the presence of a substantially homogeneous population of differentiated neural cells whereby said isolated stromal cell differentiates and acquires the phenotypic characteristics of said differentiated neural cells.

2. The method of claim 1, wherein said differentiated cells are astrocytes.

* * * * *

UNITED STATES PATENT AND TRADEMARK OFFICE
CERTIFICATE OF CORRECTION

PATENT NO.    : 6,653,134 B2
DATED         : November 25, 2003
INVENTOR(S)   : Darwin J. Prockop et al.

It is certified that error appears in the above-identified patent and that said Letters Patent is hereby corrected as shown below:

<u>Title page,</u>
Item [73], Assignee, please delete "CP Hahnemann University" to read -- MCP Hahnemann University --

<u>Column 3,</u>
Line 55, please delete "synergeneic" and replace with -- syngeneic --

<u>Column 34,</u>
Line 24, please correct claim 1 to read as follows:
-- A method of directing neural differentiation of an isolated stromel cell into a neural cell, comprising culturing said isolated stromal cell in the presence of a substantially homogeneous population of differentiated neural cells whereby said isolated stromal cell differentiates and acqujires the phenotypic characteristics of said differentiated neural cells. --

Signed and Sealed this

Eighteenth Day of May, 2004

JON W. DUDAS
*Acting Director of the United States Patent and Trademark Office*